US011253495B2

(12) United States Patent
Wang

(10) Patent No.: US 11,253,495 B2
(45) Date of Patent: Feb. 22, 2022

(54) PHARMACEUTICAL COMPOSITION FOR TREATING EXCESSIVE LACTATE PRODUCTION AND ACIDEMIA

(71) Applicant: Yanming Wang, Southborough, MA (US)

(72) Inventor: Yanming Wang, Southborough, MA (US)

( * ) Notice: Subject to any disclaimer, the term of this patent is extended or adjusted under 35 U.S.C. 154(b) by 186 days.

(21) Appl. No.: 16/654,471

(22) Filed: Oct. 16, 2019

(65) Prior Publication Data
US 2020/0155493 A1 May 21, 2020

Related U.S. Application Data

(60) Provisional application No. 62/770,355, filed on Nov. 21, 2018.

(51) Int. Cl.
| | | |
|---|---|---|
| A61K 31/198 | (2006.01) | |
| A61K 31/194 | (2006.01) | |
| A61K 31/675 | (2006.01) | |
| A61K 31/277 | (2006.01) | |
| A61P 7/00 | (2006.01) | |

(52) U.S. Cl.
CPC .......... *A61K 31/198* (2013.01); *A61K 31/194* (2013.01); *A61K 31/277* (2013.01); *A61K 31/675* (2013.01); *A61P 7/00* (2018.01); *C12Y 101/01037* (2013.01); *C12Y 101/05003* (2013.01); *C12Y 206/01001* (2013.01); *C12Y 206/01002* (2013.01)

(58) Field of Classification Search
CPC ........ C12N 9/1096; C12Y 206/001001; C12Y 206/01002; C12Y 101/05003; C12Y 101/01037
See application file for complete search history.

(56) References Cited

U.S. PATENT DOCUMENTS

| | | | |
|---|---|---|---|
| 6,036,976 A | 3/2000 | Takechi | |
| 6,866,866 B1 | 3/2005 | Chen | |
| 7,214,387 B2 | 5/2007 | Sanghvi | |
| 7,683,036 B2 | 3/2010 | Esau | |
| 7,919,116 B2 | 4/2011 | Chen | |
| 9,556,113 B2 | 1/2017 | Guan | |
| 9,611,286 B2 * | 4/2017 | Pamplona | .......... A61K 31/7135 |
| 9,750,761 B2 | 9/2017 | Kottmann | |

FOREIGN PATENT DOCUMENTS

| | | |
|---|---|---|
| CN | 96115625.2 | 1/1996 |
| EP | 2578215 | 5/2011 |
| WO | 2011/091209 | 7/2011 |
| WO | 2017/077016 | 5/2017 |

OTHER PUBLICATIONS

Krishna, S. et al., Brit, J. Pharmacol. 1996 vol. 41, pp. 29-34.*
Abruzzese F. et al. Lack of correlation between mRNA expression and enzymatic activity of the aspartate aminotransferase isoenzymes in various tissues of the rat. FEBS Letters. 1995; 366: 170-172.
Boyd JH and Walley KR. Is there a role for sodium bicarbonate in treating lactic acidosis from shock? Curr Opin Crit Care. 2008;14:379-83.
Briassouli E. and Briassoulis G. Glutamine Randomized Studies in Early Life: The Unsolved Riddle of Experimental and Clinical Studies. Clin Dev Immunol. vol. 2012; Article ID 749189; 17 pages.
Ching-Ying Wu et al. Relationship Between Blood Alcohol Concentration and Hepatic Enzymes in an Emergency Department. Tzu Chi Medical Journal 2010; 22: 24-28.
Davis EJ and Bremer J. Studies with isolated surviving rat hearts. Interdependence of free amino acids and citric-acid-cycle intermediates. Eur J Biochem. 1973 ; 38:86-97.
Dellinger RP. et al. Surviving Sepsis Campaign international guidelines for management of severe sepsis and septic shock 2008. Intensive care med. 2008;34:17-60.
DeSalles, A et al. Prognostic significance of ventricular CSF lactic acidosis in severe head injury. J Neurosurg 1986 65:615-624.
Filho RR. et al. Blood Lactate Levels Cutoff and Mortality Prediction in Sepsis—Time for a Reappraisal? A retrospective Cohort Study. Shock, 2016; 46: 480-485.
Forsythe SM and Schmidt GA. Sodium bicarbonate for the treatment of lactate acidemia. Chest. 2000;117:260-267.
Garcia-Alvarez M et al. Stress hyperlactataemia: present understanding and controversy. Lancet Diabetes Endocrinol. 2014; 2:339-47.
Jaber et al. Sodium bicarbonate therapy for patients with severe metabolic acidaemia in the intensive care unit (BICAR-ICU): a multicenter, open-label, randomized controlled, phase 3 trial. Articles (published online Jun. 14, 2018), http://dx.doi.org/10.1016/S0140-6736(18)31080-8.
Kärkelä al. Evaluation of hypoxic brain injury with spinal fluid enzymes, lactate and pyruvate. Critical care medicine. 1992; 20:3, 378-386.
Kawai M, Hosaki S. Clinical usefulness of malate dehydrogenase and its mitochondrial isoenzyme in comparison with aspartate aminotransferase and its mitochondrial isoenzyme in sera of patients with liver disease. Clin Biochem. 1990; 23:327-334.
Khosroshahi N et al. Spinal Fluid Lactate Dehydrogenase Level Differentiates between structural and metabolic etiologies of altered mental status in Children Iran J Child Neurol 2015 9:31-36.
Kim HJ. et al. Effect of Sodium Bicarbonate Administration on Mortality in Patients with Lactate Acidemia: A Retrospective Analysis. PLoS One. 2013; 8: e65283.
Kraut JA and Madias NE. Intravenous Sodium Bicarbonate in Treating patient with severe metabolic acidosis. Am J Kidney Dis. 2019; 73:572-575.
Kraut JA, and Madias NE. Lactic Acidosis: Current Treatments and Future Directions. Am J Kidney Dis. 2016; 68:473-82.
Kruse O. et al. Blood lactate as a predictor for in-hospital mortality in patients admitted acutely to hospital: a systematic review. Scand J Trauma Resusc Emerg Med. 2011; 19: 74, 12 pages.
Lampl Y et al. Cerebrospinal fluid lactate dehydrogenase levels in early stroke and transient ischemic attacks. Stroke. 1990; 21:854-857.

(Continued)

*Primary Examiner* — Heidi Reese
(74) *Attorney, Agent, or Firm* — Fish & Richardson P.C.

(57) ABSTRACT

Pharmaceuticals for treating patient with excessive lactate production and related acidemia are disclosed. Pharmaceuticals include glutamate, aspartate, BCAA, pyruvate, malate, oxaloacetate, α-ketoglutarate, AST, ALT, PLP, MDH and GPDH, Lodoxamite and Oxamate. The mechanism is that invented pharmaceuticals inhibit LDH and enhance malate/aspartate shuttle activity.

16 Claims, 16 Drawing Sheets

(56) References Cited

OTHER PUBLICATIONS

Lesu E et al. Acute liver dysfunction after cardiac arrest. PLOS One. 2018; 13(11): e0206655.
Lustig W. Activation of Alanine Aminotransferase in Serum by pyridoxal phosphate. Clin. Chem. 1977; 23:175-177.
MacDonald et al. Lactic acidosis and acute ethanol intoxication. American Journal of emergency medicine 1994, 12: 32-35.
Mattick JSA. et al. Branched Chain Amino Acid Supplementation: Impact on Signaling and Relevance to Critical Illness Wiley Interdiscip Rev Syst Biol Med. 2013; 5: 449-460.
Mesotten D, Berghe GVD. Clinical Potential of Insulin Therapy in critically ill patients. Drugs 2003 63:625-623.
Miskimins WK. et al. Synergistic anti-cancer effect of phenformin and oxamate. PLoS One. 2014; 9(1): e85576.
Mudge GH et al. Alterations of Myocardial Amino-Acid Metabolism in Chronic Ischemic Heart-Disease. Journal of Clinical Investigation, 1976; 58:1185-1192.
Nägeli M, et al. Prolonged continuous intravenous infusion of the dipeptide L-alanine—L-glutamine significantly increases plasma glutamine and alanine without elevating brain glutamate in patients with severe traumatic brain injury. Crit Care. 2014; 18:R139.
Perez-Barcena J et al. A randomized trial of intravenous glutamine supplementation in trauma ICU patients. Intensive Care Med. 2014, 40:539-547.
Prabhakaran V, Henderson AR. Unusual increases in serum lactate dehydrogenase isoenzyme-5 activity caused by severe congestive cardiac failure: two case reports. J Clin Pathol. 1979; 32:86-89.
Rao V. et al. Lactate release during reperfusion predicts low cardiac output syndrome after coronary bypass surgery. Ann Thorac Surg. Jun. 2001;71(6):1925-30.
Sanborn T et al. Augmented conversion of aspartate and glutamate to succinat during anoxia in rabbit heart. Am J Physiol. 1979 237:5 H535-541.
Schomaker S et al. Assessment of Emerging Biomarkers of Liver Injury in Human Subjects. Toxicological Sciences. 2013; 132: 276-283.
Schwartz RG et al. Regulation of Myocardial Amino-Acid Balance in the Conscious Dog. Journal of Clinical Investigation, 1985; 75:1204-1211.
Stehle P and Kuhn, K.. et al. Glutamine: An Obligatory Parenteral Nutrition Substrate in Critical Care Therapy. Biomed Res Int. 2015; 2015: 545467.
Taegtmeyer H et al. De Novo alanine synthesis in isolated oxygen-deprived rabbit myocardium. Journal of Biological Chemistry. 1977; 252:5010-5018.
Vaagenes P. et al. Brain Enzyme Levels in CSF After Cardiac Arrest and Resuscitation in Dogs: Markers of Damage and predictors of outcome. J Cereb Blood Flow Metab. 1988 8:262-275.
Vanderlinde RE. Review of pyridoxal phosphate and the transaminases in liver disease. Ann Clin Lab Sci. 1986; 16:79-93.
Velissaris D. et al. The Use of Sodium Bicarbonate in the Treatment of Acidosis in Sepsis A Literature Update on a Long Term Debate. Crit Care Res Pract. Epub Jul. 30, 2015.
Wischmeyer PE et al. Parenteral glutamine supplementation in critical illness: a systematic review Crit Care. 2014; 18: R76.

\* cited by examiner

PHARMACEUTICAL COMPOSITION FOR TREATING EXCESSIVE LACTATE PRODUCTION AND ACIDEMIA

CROSS-REFERENCE TO RELATED APPLICATION

This application claims priority to U.S. Provisional Application No. 62/770,355, filed Nov. 21, 2018, the contents of which are hereby incorporated by reference in their entirety.

TECHNICAL FIELD

This disclosure relates to the field of clinical medicine. In particular, the present disclosure relates to the use of pharmaceuticals to treat patient with excessive lactate production and related acidemia.

BACKGROUND

Cells in human body mainly use glucose as fuel substrate to generate energy (ATP, adenosine triphosphate) in a two-step process, i.e., the anaerobic glycolysis and the oxidative phosphorylation or the Krebs cycle (also known as citric acid cycle or tricarboxylic acid cycle). The glycolysis takes place in cytoplasm and does not need oxygen, glucose is broken down to the pyruvate, and then to the lactate. The oxidative phosphorylation takes place in mitochondria and needs oxygen, the pyruvate is converted to acetyl CoA to enter Krebs cycle, intermediates of Krebs cycle are oxidized to water and carbon dioxide.

Excessive lactate production is caused by increased glycolysis during glucose metabolism. Instead converting it to acetyl CoA, more pyruvate is converted to the lactate. Without conversion of pyruvate to acetyl CoA, Krebs cycle can not be initiated. Compared with Krebs cycle, glycolysis is not an efficient way to yield ATP, therefore, a cell with excessive lactate production is associated with ATP scarcity. The ATP is energy current for all living cells in the body. Without sufficient ATP, cells disfunction and eventually die. ATP scarcity is the final common pathway of all diseases before death. Excessive lactate production can be regarded an indicator of cellular ATP scarcity.

In clinic, excessive lactate production is a pathological process of various diseases, particularly critically ill patients. Excessive lactate production from affected cells releases into the blood. It is frequently manifested by hyperlactatemia in clinic. Hyperlactatemia refers to lactate concentration higher than 2 mmol/L in the blood. Severe hyperlactatemia is often accompanied by acidemia, also known as lactate acidemia or lactate acidosis which refers to blood pH less than 7.35. The acidemia further interferes with cellular biochemical reactions of the body aggravating abnormal metabolism. Hyperlactatemia and acidemia can be easily detected by simple measurement of blood. However, if excessive lactate production is only confined to the part of affected organ or if excessive lactate production is not severe enough, the hyperlactatemia and acidemia may not be easily detected by simple the blood testing.

Hyperlactatemia and lactate acidemia are ominous signs in clinic. For examples, patients with lactate level of more than 5 mmol/L have shown a high mortality rate. Patient with sepsis has poor prognosis when lactate level more than 2.5 mmol/L. However, effective treatment of hyperlactatemia is not available so far. Sodium bicarbonate ($NaHCO_3$) has been used to treat lactate acidemia. Although $NaHCO_3$ can increase blood pH value, evidences have shown that it has very limited effect or even aggravating outcome for patient with lactate acidemia.

The lactate dehydrogenase (LDH), the enzyme that is responsible for lactate formation, is mainly in cytosol. It catalyzes conversion of the pyruvate to the lactate at a cost of turning NADH (reduced nicotinamide adenine dinucleotide) to $NAD^+$ (oxidized nicotinamide adenine dinucleotide) (Pyruvate+$NADH^+$→Lactate+$NAD^+$). The energy from glycolysis is transferred to the NADH through NAD+. The NADH has potential to generate ATP. However, NADH produced in the cytosol cannot directly enter the mitochondrial matrix to generate ATP. Regeneration of NAD+ is critical for continuation of glycolysis. Therefore, enhanced LDH enzymatic reaction wastes NADH energy potential and eventually leads to lactate accumulation. Normal serum LDH may range about 60-450 units/L (Newborn: 160 to 450 Units/L, Infant: 100 to 250 units/L, Child: 60 to 170 units/L, and Adult: 100 to 190 units/L). The LDH is frequently tested and widely used as an indicator for tissue damage in clinic. The LDH activity is often up-regulated in many diseases, both acute and chronic. Increased LDH activity invariably parallel to excessive lactate production. The lactate is generally considered as a glycolytic end product, and most cells can not use it to produce ATP. It can only be converted back to glucose in liver via Cori cycle which consumes ATP.

The oxamate, a salt of oxamic acid, is a non-competitive inhibitor of LDH. Its molecular formula is $C_2H_2NO_3^-$, its molecular weight is 88.042. The oxamate can reduce lactate production by inhibiting LDH. The oxamate has only been proposed for cancer therapy.

The lodoxamide is a Mast cell stabilizer. Ophthalmic lodoxamide Tromethamine (Alomide) is used to treat redness, burning, itching and swelling of the eyes that is caused by allergic reactions.

Malate dehydrogenase (MDH, EC 1.1.1.37) is the key enzyme in the malate/aspartate shuttle. NADH is oxidized to $NAD^+$ by the cytosolic MDH (MDH1), while oxaloacetate is simultaneously reduced to malate. The malate penetrates the mitochondrial inner membrane. Inside the matrix, the malate is converted to oxaloacetate by mitochondrial MDH (MDH2), generating the NADH, which then transfers electrons to the electron transport chain (ETC) in mitochondria. In this way, cytoplasmic reducing power of NADH is transferred to enter the ETC to generate ATP molecules in mitochondria. MDH is highly abundant in vital organs such as liver, heart, muscle and brain etc. It is estimated that the normal serum MDH may range about 79-176 units/L. The MDH activity are reportedly increased mainly in chronic diseases, such as liver cirrhosis. The MDH is not frequently tested in clinic.

Glycerol-3-phosphate dehydrogenase (GPDH, EC 1.1.1.8) is the key enzyme in the glycerol phosphate shuttle. NADH is oxidized to $NAD^+$ by the cytosol GPDH, while dihydroxyacetone phosphate is simultaneously reduced to glycerol-3-phosphate. Glycerol-3-phosphate gets converted back to dihydroxyacetone phosphate by an inner membrane-bound mitochondrial GPDH simultaneously reducing FAD to $FADH_2$. In this way, cytoplasmic reducing power of NADH is transferred to enter the ETC to generate ATP molecules in mitochondria. The GPDH activity are reportedly increased mainly in chronic diseases, such as liver cirrhosis. The GPDH is seldom tested in clinic.

Transaminase, also known as aminotransferases, are enzymes that catalyze a transamination reaction between an amino acid and an α-keto acid. In transamination, the $NH_2$ group on one molecule is exchanged with the =O group on the other molecule. The amino acid becomes a keto acid, and the keto acid becomes an amino acid. The reactions are readily reversible, the direction being determined by which of the reactants are in excess.

Two most important transaminases associated with the malate/aspartate shuttle activity are Aspartate Transaminase (AST, EC 2.6.1.1), also known as glutamic oxaloacetic transaminase (GOT), and Alanine Transaminase (ALT, EC 2.6.1.2), also known as glutamic pyruvate transaminase (GPT). The pyridoxal 5'-phosphate (PLP), also known as active form of Vitamin B6, is the co-enzyme of these two transaminases. The products of enzymatic reaction catalyzed by these two transaminases include aspartate, glutamate, α-ketoglutarate, oxaloacetate and pyruvate.

AST has two isoenzymes, GOT1 or cAST is cytosolic isoenzyme, and GOT2 or mAST is mitochondrial isoenzyme.

AST and ALT are found in various body tissues, including the liver, heart, skeletal muscle, kidneys, brain, and red blood cells etc. In clinic, The AST and ALT are frequently tested in clinic. It is estimated that the normal AST content may range 10-40 units/L, and normal ALT content may range 7-56 units/L. Serum AST and ALT are elevated in many diseases. For examples, there are marked increases of serum AST and ALT in circulatory failure, such as hemorrhagic shock, cardiac arrest, heart failure, and various organ damages, such as hepatitis, kidney disease, brain diseases etc. There are marked increases of serum AST and ALT even in healthy individual with intensive exercise. Although the elevation of AST and ALT can occur in almost all types of organs in response to various damages, they do have some preference to organ. In fact, serum AST elevation is regarded as broader biomarkers of tissue damage, and ALT elevation is more related to liver diseases. It usually takes hours to days for these enzymes to be increased in responding to initial injury. In some patient, transaminase activity simply does not increase despite of elevated mRNA level of transaminase.

Glutamate or glutamine plays a pivotal role in the conversion among amino acids, intermediates of Krebs cycle and malate/aspartate shuttle. Glutamic acid consists of two carboxyl groups (—COOH) and an amine group (—$NH_2$) (molecular formula: $C_5H_9NO_4$; molecular weight:147.13). It has very limited solubility in water (only 8.6 mg/ml at 25° C.). Glutamine is similar to glutamic acid, except the carboxylic group is replaced by an amide (molecular formula: $C_5H_{10}N_2O_3$; molecular weight: 146.14). Glutamate is the salt of glutamic acid, such as monosodium glutamate (molecular formula: $C_5H_8NNaO_4$; molecular weight: 169.11), Magnesium diglutamate (molecular formula: $C_{10}H_{16}MgN_2O_8$; molecular weight: 388.62). Glutamic acid, glutamate and glutamine often collectively refer to glutamate as they are easily interchangeable chemically inside body.

Glutamate is used to reduce blood ammonia to treat hepatic encephalopathy in clinic. Ammonia can be detoxified by reacting with glutamate or glutamic acid to form glutamine. For example, the pharmaceutical preparation of sodium glutamate injection usually contains 5.75 g in each 20 ml vial. The pH value of this pharmaceutical preparation concentration is between 7.5-8.5.

Normal serum glutamic acid and glutamine range about 18-140 μmol/L and 390-730 μmol/L respectively. Normal serum aspartic acid and asparagine range about 0-26 μmol/L and 15-130 μmol/L respectively.

In clinic, serum glutamine and glutamate concentration are often reduced or even be depleted very quickly in many patients, particularly critically ill patients. Contrary to the decrease of glutamate, alanine concentration is often increased in patients with excessive lactate production. The increased ratio of Alanine/Glutamate was reportedly used as an index of reversibility of tissue damage. The alanine is shuttled to the liver where the nitrogen enters the urea cycle or consume α-ketogiutarate to generate pyruvate to make glucose which is known as alanine cycle, glucose-alanine cycle or Cahill cycle. This cycle consumes ATP. Therefore, alanine is not beneficial to or may even aggravate the outcome. However, glutamate is often mistakenly combined with alanine, for examples, almost all amino acid nutrition infusion products contain L-alanine. Dipeptiven® (Fresenius Kabi), a dipeptide containing L-alanine and -glutamine, is available in clinic to treat critically ill patients. The results of Dipeptiven® treatment have been controversial. For examples, Wischmeyer PE (Glutamine: Mode of action in critical illness. Crit Care Med 2007 Vol. 35, No. 9 (Suppl.), 5541-5544) reported beneficial effect; Heyland (A Randomized Trial of Glutamine and Antioxidants in Critically Ill Patients N Engl J Med. 2013; 368(16):1489-97) and Chen (The effect of glutamine therapy on outcomes in critically ill patients: a meta-analysis of randomized controlled trials. Crit Care. 2014; 18(1): R8.) reported negative effects.

Many amino acids can be converted to glutamate or glutamine, and can be used as fuel to generate ATP as well. Amino acids in human body can be categorized into essential (including Histidine, Isoleucine, Leucine, Lysine, Methionine, Phenylanine, Threonine, Tryptohan and Valine), non-essential amino acid (Alanine, Aspartic acid, Asparagine, Glutamic acid, Serine, Selenocysteine and Pyrrolysine), and conditionally essential (including Arginine, Cysteine, Glutamine, Glycine, Proline and Tyrosine). Conditionally essential amino acid cannot be synthesized under pathophysiological conditions such as trauma, sepsis, surgery, wound, severe catabolic distress.

Leucine, Isoleucine and Valine belong to branched-chain amino acid (BCAA) which has an aliphatic side chain with a branch. The final catabolic products of BCAA are acetyl-CoA and succinyl-CoA, which can enter Krebs cycle for ATP production. In clinic, serum BCAA is often decreased or depleted in patients associated with hyperlactatemia.

Currently amino acid injections are mainly for intravenous nutritional supplement. Pharmaceutical companies manufacturing amino acid injections include Baxter, B Braun, Clintec Nutrtion, Hospira, ICU Medical, Fresenius Kai etc. Their products include Glycine, Prosol, Aminosyn, Clinimix, FreAmine, HepatAmine, Hepatasol, Kabiven, Novamine, Nutrinea, Olimel, Perikabiven, Plenamine, Smofkabiven, Travasol, Trophamine, Vamin etc. These amino acid formulations usually contain large amount of alanine, D-glucose or lipid. Mounting evidence have also shown that D-glucose and lipid can aggravate hyperlactatemia and lactate acidemia.

In central nervous system (CNS), glutamate and aspartate are excitatory amino acid neurotransmitters. Current dogmatic theory considers glutamate and aspartate as excitotoxin that can destroy CNS tissue by excessive activation of glutamate receptors such as the N-methyl-D-aspartate receptor (also known as the NMDA receptor). The excessive NMDA receptor activity causes calcium ions ($Ca^{2+}$) to influx into cells. High $Ca^{2+}$ concentrations activate a cascade of cell degradation processes such as proteases, lipases, nitric oxide synthase, free radicals leading to cell death. Overwhelming studies have reported glutamate and aspartate release after various injuries to brain and spinal cord. Therefore, persons skilled in the art believe that glutamate damages brain tissue and mediate a wide range of neurologic diseases, such as brain hypoxia-ischemia, trauma etc. In spite of glutamate usage in peripheral organ systems, persons skilled in the art have been trying to avoid the glutamate in neurological diseases because of the concern of prevailing excitotoxicity theory and reports that glutamate administration may induce brain damage due to its excitotoxic and edema-aggravating potential.

SUMMARY

Accordingly, the instant invention discloses that the oxamate, a non-competitive inhibitor of LDH, can be used as pharmaceutical composition to treat a patient with excessive lactate production and lactate acidemia. The lodoxamide has two similar chemical groups as the oxamate, it can also inhibit LDH, and can be used as in a pharmaceutical composition to treat patient with excessive lactate production and lactate acidemia.

The dosage of the oxamate and lodoxamide is generally in the range of about 0.00001-1,000 mg/kg body weight, specifically in the range of about 1-100 mg/kg body weight. The route of administration can be oral, intravenous or intramuscular injection, the preferred route is intravenous or intramuscular injection.

The inventor has also surprisingly discovered that amino acids (except alanine), particularly, glutamate, aspartate, BCAA can reduce lactate production. The malate, oxaloacetate, pyruvate and α-ketoglutarate can also reduce lactate production.

One side effect of sodium glutamate injection is alkalemia in clinic. The sodium and potassium salt of malate, oxaloacetate, aspartate, glutamate, pyruvate and α-ketoglutarate have higher pH value, can lead to alkalosis in blood. This is because sodium and potassium salts of these substrates are salt of strong base and weak acid. Therefore, sodium and potassium salts in this invention are especially useful to formulate pharmaceutical compositions, because they not only reduce lactate but also correct acidemia. For example, pharmaceutical preparation of sodium glutamate 5.75 g in each 20 ml water, the pH value is between 7.5-8.5. Unexpectedly, the inventor found that this preparation can be used for increasing blood pH value to correct acidemia.

The inventor has also surprisingly discovered that in contrary to current excitotoxic theory, glutamate, glutamine and aspartate can be used to reduce lactate production and ameliorate lactate acidemia in all neurological diseases too, particularly cerebral ischemia, brain trauma.

The dose of amino acids or malate, oxaloacetate, pyruvate and α-ketoglutarate can range between 0.001 to 10 g/kg, specifically in the range of about 0.1-3 g/kg.

The inventor has also surprisingly discovered that the MDH, GPDH, AST, ALT, PLP (or Vitamin B6) and their substrates all can be used as pharmaceutical composition to treat patients with excessive lactate production and lactate acidemia.

To reduce the amount of NADH in cytosol, two pathways are recruited, i.e. the shuttles and the LDH catalyzed reaction. The shuttles include malate/aspartate shuttle and the glycerol phosphate shuttle. These shuttles can bring cytosolic reducing equivalents into the mitochondrial matrix, without NADH itself actually entering the matrix. The malate/aspartate shuttle activity involves coupled transaminase reaction with cytosolic and mitochondrial transamination, and shares substrates including aspartate, glutamate, oxaloacetate, α-ketoglutarate and pyruvate. Unlike the LDH, the MDH and GPDH activity are not increased quickly enough in many acute pathological conditions. The AST and the ALT are not increased quickly enough either in many acute pathological conditions.

MDH, GPDH, AST, ALT, PLP (or Vitamin B6) and their substrates can compete with the LDH by enhancing malate/aspartate shuttle activity. Enhanced transamination reaction catalyzed by the AST and ALT orchestrates enhanced malate/aspartate shuttle. This is the new mechanism to reduce lactate production and ameliorate lactate acidemia. NADH is oxidized to $NAD^+$ by the cytosolic MDH, and the oxaloacetate is needed to produce malate. Malate enters mitochondria. By this way, the cytosolic MDH compete with LDH for consuming NADH, the more NADH is used to form malate, the less NADH is consumed to form lactate, hence lactate production and lactate acidemia can be reduced by enhanced malate/aspartate shuttle activity.

Accordingly, the instant invention discloses MDH, GPDH, AST, ALT, PLP as a pharmaceutical component to treat patients with excessive lactate production and lactate acidemia.

Accordingly, the instant invention also discloses the combination of MDH, GPDH, AST, ALT, PLP, their substrates and amino acids as pharmaceutical compositions to treat patients with excessive lactate production and lactate acidemia. The combination is advantageous because it can promote the substrate enzymatic reaction and enhance malate/aspartate shuttle. The AST and ALT catalyzed enzymatic reactions produces oxaloacetate, aspartate, glutamate and α-ketoglutarate. These enzymatic reactions are tightly linked with malate formation and malate/aspartate shuttle. Exogenous oxaloacetate, malate, aspartate, glutamate and α-ketoglutarate and amino acids can replenish substrate consumption. Therefore, their combination can further promote malate/aspartate shuttle, lead to synergetic effect, and maintain long efficacy. Any combination may be chosen. Examples of these combination are: MDH+AST; MDH+ALT; MDH+AST+ALT; MDH+AST+glutamate; MDH+ALT+glutamate; MDH+AST+PLP+glutamate; MDH+ALT+PLP+glutamate; MDH+oxaloacetate, AST+glutamate; ALT+glutamate; AST+glutamate+Aspartate; ALT+glutamate+pyruvate; AST+PLP+glutamate; ALT+PLP+glutamate; MDH+malate oxaloacetate+glutamate+aspartate+α-ketoglutarate; GPDH+AST; GPDH+ALT; GPDH+AST+ALT; GPDH+AST+glutamate; GPDH+ALT+glutamate; GPDH+AST+PLP+glutamate; GPDH+ALT+PLP+glutamate; AST+oxaloacetate+glutamate+aspartate+α-ketoglutarate; ALT+oxaloacetate+glutamate+aspartate+ketoglutarate pyruvate; Malate+oxaloacetate+glutamate+aspartate+α-ketoglutarate+pyruvate BCAA etc. The preferred combinations are MDH+AST, MDH+AST+glutamate, MDH+oxaloacetate, AST+glutamate, AST+glutamate+aspartate, Glutamate+aspartate etc.

The MDH, GPDH, AST, ALT can come from animal extract or can be manufactured by bioengineering recombinant protein technology.

The dosage of the MDH, GPDH, AST, and ALT is generally in the range of about 1-100,000 units/kg body weight or 0.0001 ng to 1 g/kg body weight, specifically in the range of about 1-1,000 units/kg body weight or 0.01 ng to 0.01 g/kg body weight. The dose of PLP can be in a range about 1-1000 mg/kg, specifically in the range of about 1-100 mg/kg.

The preferred route of the MDH, GPDH, AST, ALT, substrates and amino acids is intravenous or intramuscular injection.

The magnesium is cytoprotective. It has synergetic effect and can be used to formulate pharmaceutical compositions too. For example, magnesium oxide, magnesium sulfate, magnesium chloride can be used to form magnesium salt of malate, oxaloacetate, aspartate, glutamate, pyruvate and α-ketoglutarate. The $Mg^{2+}$ can be used to formulate the pharmaceutical compositions of MDH, GPDH, AST, ALT and PLP.

One feature of the instant invention is a method for treating a patient having excessive lactate production or lactate academia. The method includes administering to the patient in need thereof an effective amount of at least one substance selected from the group consisting of glutamate, aspartate, BCAA, malate, pyruvate, oxaloacetate, α-ketoglutarate, AST, ALT, PLP, MDH, GPDH, Oxamate, Lodoxamite and salts thereof.

In some embodiments, the substance can be administered at a dosage of from at least 10 ng (e.g., at least 100 ng, at least 1 µg, at least 10 µg, at least 100 µg, at least 1 mg, at least 0.005 g, at least 0.01 g, at least 0.05 g, at least 0.1 g, at least 0.5 g, or at least 1 g) per kilogram body weight to at most 10 g (e.g., at most 8 g, at most 6 g, at most 5 g, at most 4 g, at most 2 g, at most 1 g, at most 0.5 g, at least 0.1 g, at least 0.05 g, or at least 0.01 g) per kilogram body weight.

Another feature of the instant invention is that MDH, GPDH, AST, ALT, PLP, their substrates and their combination can be used to treat patients with excessive lactate production and lactate acidemia caused by ischemia/reperfusion injury. The treatment can begin prior to blood reperfusion. The treatment can last for a suitable period, for example, 5 minutes to 3 hours to allow ischemia issue to generate enough ATP, then restore blood flow to the ischemic region. This is particularly useful when treating patient with thrombolytic therapy (such as tissue plasminogen activator, tPA), percutaneous aspiration thrombectomy or angioplasty etc. In some embodiments, the MDH, GPDH, AST, ALT, PLP, their substrates or their combination can be administered at a dosage of from at least 0.0001 ng (e.g., at least 0.001 ng, at least 0.01 ng, at least 0.1 ng, at least 1 ng, at least 10 ng, at least 100 ng, at least 1 µg, at least 10 µg, at least 100 µg, or at least 1 mg) per kilogram body weight to at most 1 g (e.g., at most 0.8 g, at most 0.6 g, at most 0.5 g, at most 0.4 g, at most 0.2 g, at most 0.1 g, at most 0.05 g, or at most 0.01 g) per kilogram body weight.

Another feature of the instant invention is that glutamate, glutamine, aspartate and their combination with MDH, GPDH, AST, ALT and PLP (or vitamin B6) can be used to treat patients with neurological diseases having excessive lactate production and lactate acidemia, although this is contrary to current excitotoxic theory that glutamine, glutamate and aspartate are excitotoxin to neuronal tissue.

DETAILED DESCRIPTION

Figure 1:
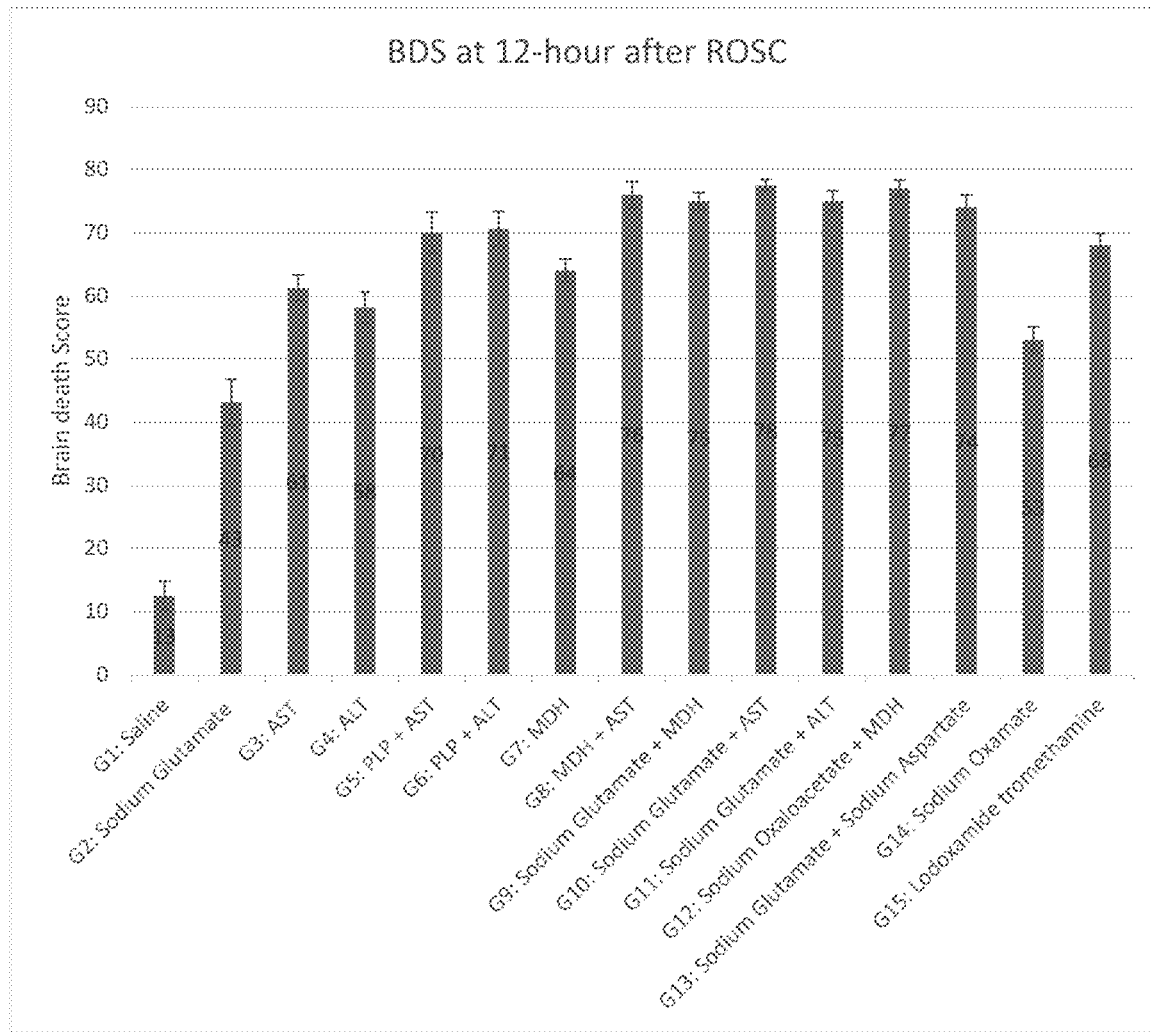
FIG. 1 is a graph showing the effects of treatment groups G1-G15 on the brain death score (BDS) at 12-hour after return of spontaneous circulation (ROSC) in a cardiac arrest rat model.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The term "amino acid" is art-recognized and refers to all compounds, whether natural or synthetic, which include both an amino functionality and an acid functionality, including amino acid analogs and derivatives. The names of the amino acids are abbreviated herein in accordance with the recommendations of IUPAC-IUB. The term "amino acid" is used herein also refers to salt or ester of amino acid, for example, glutamic acid also refers to sodium glutamate and glutamine.

The term "MDH" as used herein is art-recognized and refers to an abbreviation of malate dehydrogenase.

The term "GPDH" as used herein is art-recognized and refers to an abbreviation of glycerol-3-phosphate dehydrogenase.

The term "Transaminase" as used herein is art-recognized and refers to any enzymes that catalyze a transamination reaction between an amino acid and an α-keto acid.

The term "AST" as used herein is art-recognized and refers to an abbreviation of Aspartate Transaminase which is also known as glutamic oxaloacetic transaminase (GOT).

The term "ALT" as used herein is art-recognized and refers to an abbreviation of Alanine Transaminase which is also known as glutamic pyruvate transaminase (GPT).

The term "PLP" as used herein is art-recognized and refers to an abbreviation of pyridoxal 5'-phosphate which is also known as active form of Vitamin B6 is the co-enzyme of transaminases.

The term "substrates" as used herein is art-recognized and refers to substrates of enzymatic reaction for malate/aspartate shuttle, AST, ALT, and intermediate of Krebs circle. Specifically, substrates include the malate, oxaloacetate, aspartate, glutamate, pyruvate and α-ketoglutarate.

The term "administering" includes any method of delivery of a compound of the present invention, including but not limited to, a pharmaceutical composition or therapeutic agent, into a subject's system or to a particular region in or on a subject. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration. "Parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The terms "comprise" and "comprising" are used in the inclusive, open sense, meaning that additional elements may be included.

The term "including" is used to mean "including but not limited to". "Including" and "including but not limited to" are used interchangeably.

A "patient," "subject" or "host" to be treated by the subject method may mean either a human or non-human animal.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) other non-toxic compatible substances employed in pharmaceutical formulations; and (22) artificial cerebrospinal fluid.

The term "pharmaceutically-acceptable salts" is art-recognized and refers to the relatively non-toxic, inorganic and organic acid addition salts of compounds, including, for example, those contained in compositions of the present invention.

The term "prophylactate" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactate, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "purified" refers to an object species that is the predominant species present (i.e., on a molar basis it is more abundant than any other individual species in the composition). Generally, a purified composition will have one species that comprises more than about 80 percent of all species present in the composition, more than about 85%, 90%, 95%, 99% or more of all species present. The object species can be purified to essential homogeneity (contaminant species cannot be detected in the composition by conventional detection methods) wherein the composition consists essentially of a single species. A skilled artisan can purify an enzyme or amino acid of the invention using standard techniques for purification. Purity of an enzyme or amino acid can be determined by a number of methods known to those of skill in the art, including for example, amino-terminal amino acid sequence analysis, gel electrophoresis, mass-spectrometry analysis. etc.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention can be administered in a sufficient amount to produce a at a reasonable benefit/risk ratio applicable to such treatment.

The term "critically ill" refers to any disease that need immediate treatment, including, but not limited to hypoxia, ischemia, trauma, and poisoning etc.

The term "treat or treating" is art-recognized and refers to curing as well as ameliorating at least one symptom of any condition or disease.

Inhibition of LDH activity reduces lactate production and ameliorates lactate acidemia. The Oxamate has only been reported for use in cancer therapy as LDH inhibitor. The inventor surprisingly discovered that lodoxamide can also inhibit LDH activity. The instance invention uses oxamate, and lodoxamide to inhibit of LDH activity as pharmaceutical components to treat patients with excessive lactate production and lactate acidemia. Lodoxamide Tromethamine (Alomide) is a Mast cell stabilizer, 0.1% Lodoxamide Tromethamine solution has been used to treat redness, burning, itching and swelling of the eyes that is caused by allergic reactions. it is advantageous to re-purpose the use of Lodoxamide Tromethamine as it has large amount safety data in human.

The oxamate and lodoxamide are all commercially available. To treat a patient with excessive lactate production and lactate acidemia, effective amount of oxamate or lodoxamide can be administered. The dosage of the oxamate and lodoxamide is generally in the range of about 0.00001-1,000 mg/kg body weight, specifically in the range of about 1-100 mg/kg body weight. The route of administration can be oral, intravenous or intramuscular injection, the preferred route is intravenous or intramuscular injection. Special drug delivery technique may be needed, particularly if oral administration is given, such as enteric coating, slow release.

The inventor has also surprisingly discovered that amino acids (except alanine), particularly, glutamate, aspartate and BCAA can be used as pharmaceutical components to treat patients with excessive lactate production and lactate acidemia. The malate, oxaloacetate, pyruvate and α-ketoglutarate can also be used as pharmaceutical components to treat patients with excessive lactate production and lactate acidemia.

The sodium and potassium salts of these amino acids, malate, oxaloacetate, pyruvate and α-ketoglutarate have higher pH value, can lead to alkalosis in blood. This is because sodium and potassium salts of these substrates are salts of strong base and weak acid. Therefore, sodium and potassium salts in this invention are especially useful to formulate pharmaceutical compositions, because they not only reduce lactate but also correct acidemia. For example, pharmaceutical preparation of sodium glutamate 5.75 g in each 20 ml water, the pH value is between 7.5-8.5. this preparation can be used for increasing blood pH value to correct acidemia and reducing lactate production.

The inventor has also surprisingly discovered that in contrary to current excitotoxic theory, glutamate, glutamic acid, glutamine and aspartate can be used to treat all neurological diseases with lactate production and lactate acidemia, particularly cerebral ischemia, brain trauma.

The dose of these amino acids, malate, oxaloacetate, pyruvate and α-ketoglutarate can range between 0.001 to 10 g/kg, specifically in the range of about 0.1-3 g/kg.

The inventor has surprisingly discovered that enhancement of malate/aspartate shuttle or glycerol phosphate shuttle activity can reduce lactate production and ameliorate lactate acidemia. The MDH, GPDH, AST, ALT, PLP (or Vitamin B6) and their substrates orchestrate malate/aspartate shuttle activity and glycerol phosphate shuttle activity. Therefore, they all can be used to treat patients with excessive lactate production and lactate acidemia.

The cytosol MDH catalyzes the conversion of oxaloacetate to malate.

Oxaloacetate+NADH+H$^+$→Malate+NAD$^+$.

The mitochondrial MDH catalyzes the conversion of malate to oxaloacetate.

Malate+NAD$^+$→Oxaloacetate NADH+H$^+$

The cytosol GPDH catalyzes the conversion of Phosphate dihydroxyacetone to Glycerol-3-phosphate.

Phosphate dihydroxyacetone+NADH+H$^+$→Glycerol-3-phosphate+NAD$^+$.

The mitochondrial GPDH catalyzes the conversion of Glycerol-3-phosphate to Phosphate dihydroxyacetone.

Glycerol-3-phosphate+NAD$^+$→Phosphate dihydroxyacetone→NADH+H$^+$

The AST catalyzes the conversion of oxaloacetate and glutamate to aspartate and α-ketoglutarate.

Oxaloacetate+glutamate ⇌ Aspartate+α-ketoglutarate

The ALT, catalyzes the interconversion of alanine and α-ketoglutarate to pyruvate and glutamate.

Alanine+α-ketoglutarate ⇌ pyruvate+glutamate.

In clinic, these enzymes usually are elevated in blood. For examples, the AST and ALT are considered as biomarkers released from organ damages. The inventor, however, has surprisingly discovered that the elevation of these enzymes in serum is an endogenous protective mechanism in response to abnormal glucose metabolism and excessive lactate production and lactate acidemia. It usually takes hours or days for them to rise in serum depending on the causes and individual condition.

Accordingly provided are pharmaceuticals to treat patients with excessive lactate production and lactate acidemia comprising of MDH, GPDH, AST, ALT, PLP.

The MDH, GPDH, AST, ALT can be extracted from animal source or can be manufactured by bioengineering recombinant protein technology. The methods of which, the isolation and the purification process are well-known to those of skill in the art. The PLP is commercially available.

For better treatment results, the MDH, GPDH, AST, ALT, PLP and their substrates can be combined. The MDH, GPDH, AST, ALT and PLP catalyzing enzymatic reactions share similar substrates, and are tightly linked with malate formation, malate/aspartate shuttle and Krebs circle. Exogenous enzymes and substrates can replenish their consumption. Therefore, their combination can further enhance malate/aspartate shuttle activity, lead to synergetic effect, and maintain long efficacy. The combination can be any of MDH, GPDH, AST, ALT, PLP and their substrates or amino acids mixture. Their substrates including malate, oxaloacetate, aspartate, glutamate, pyruvate and α-ketoglutarate are commercially available. Except alanine, all amino acids can be chosen as substrates too. Glutamine, glutamate, aspartate, malate, BCAA, oxaloacetate, α-ketoglutarate and pyruvate are preferred. Glutamate, glutamine and aspartate play a pivotal role in the conversion among amino acids, and malate/aspartate shuttle, therefore are most preferred.

It is preferred that they are chosen according to specific substrates-enzymatic reaction. Examples of combination include: MDH+AST; MDH+ALT; MDH+AST+ALT; MDH+AST+glutamate; MDH+ALT+glutamate; MDH+AST+PLP+glutamate; MDH+ALT+PLP+glutamate; MDH+oxaloacetate, AST+glutamate; ALT+glutamate; AST+glutamate+Aspartate; ALT+glutamate+pyruvate; AST+PLP+glutamate; ALT+PLP+glutamate; MDH+malate+oxaloacetate+glutamate+aspartate+α-ketoglutarate; GPDH+AST; GPDH+ALT; GPDH+AST+ALT; GPDH+AST+glutamate; GPDH+ALT+glutamate; GPDH+AST+PLP+glutamate; GPDH+ALT+PLP+glutamate; AST+oxaloacetate+glutamate+aspartate+α-ketoglutarate; ALT+oxaloacetate+glutamate+aspartate+α-ketoglutarate pyruvate; Malate+oxaloacetate+glutamate+aspartate+α-ketoglutarate+pyruvate+BCAA etc. The preferred combinations are MDH+AST, MDH+AST+glutamate, MDH+oxaloacetate, AST+glutamate, AST+glutamate+aspartate, Glutamate+aspartate etc.

Alternatively, the MDH, GPDH, AST, ALT, PLP and their substrates and amino acids can be packed separately. When a patient needs treatment, combination can be made by mixing them before administration. They can also be used as a treatment method, to be administered individually, the combination occurs inside the body of a patient.

The dosage of the subject MDH, GPDH, AST, and ALT can generally be in the range of about 1-100,000 units/kg body weight or 0.0001 ng to 1 g/kg body weight, specifically in the range of about 1-1,000 units/kg body weight or 0.01 ng to 0.01 g/kg body weight. The dose of PLP can be in the range of about 1-1000 mg/kg, specifically in the range of about 1-100 mg/kg. The dose of substrates or amino acids can range between 0.001 and 10 g/kg, specifically in the range of about 0.1-3 g/kg. The route of administration can be oral, intravenous or intramuscular injection, the preferred route is intravenous or intramuscular injection. Special drug delivery technique may be needed, particularly if oral administration is given, such as enteric coating, slow release.

The oxamate and lodoxamide can be formulated into pharmaceutical compositions suitable for administration to a subject. The MDH, GPDH, AST, ALT, PLP, their substrates, amino acids, and their combination can be formulated into pharmaceutical compositions suitable for administration to a subject. Such pharmaceuticals or compositions can additionally comprise wetting agents, emulsifiers and lubricants, such as sodium lauryl sulfate and magnesium stearate. In addition, coloring agents, release agents, coating agents, sweetening, flavoring and perfuming agents, preservatives and antioxidants can be present in the formulated agents.

The magnesium is cytoprotective. It has synergetic effect and can be used to formulate pharmaceutical compositions in this invention. For example, magnesium oxide, magnesium sulfate, magnesium chloride can be used to form magnesium salt of malate, oxaloacetate, aspartate, glutamate, pyruvate and α-ketoglutarate. $Mg^{2+}$ can be used to formulate the pharmaceutical compositions of MDH, GPDH, AST, ALT and PLP.

Subject pharmaceuticals can be suitable for oral, nasal, topical (including buccal and sublingual), rectal, vaginal, aerosol and/or parenteral administration. The formulations can conveniently be presented in unit dosage form and can be prepared by any methods well known in the art of pharmacy. The amount of composition that can be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention can also be administered as a bolus, electuary, or paste.

In solid dosage forms for oral administration (capsules, tablets, pills, dragees, powders, granules and the like), the subject composition can be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the compositions can also comprise buffering agents. Solid compositions of a similar type can be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the subject composition moistened with an inert liquid diluent. Tablets, and other solid dosage forms, such as dragees, capsules, pills and granules, can optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms can contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, can contain suspending agents such as ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for transdermal administration of a subject composition includes powders, sprays, ointments, pastes, creams, lotions, gels, solutions, patches and inhalants. The active component can be mixed under sterile conditions with a pharmaceutically acceptable carrier, and with any preservatives, buffers, or propellants which may be required.

The ointments, pastes, creams and gels can contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which can be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which can be employed in the pharmaceutical compositions of the invention include water, saline, artificial cerebrospinal fluid, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further provided are method to treat patients with excessive lactate production and lactate acidemia using above formulated pharmaceuticals.

To identify a patient with excessive lactate production and lactate acidemia, a small amount of blood can be withdrawn to test blood lactate and pH value. In clinic, hyperlactatemia refers to lactate concentration higher than 2 mmol/L in the blood. Lactate acidemia refers to blood pH less than 7.35 when hyperlactatemia occurs. Once the testing confirms hyperlactatemia or lactate acidemia, treatment should start as soon as possible. It is well-known to those of skill in the art that in many diseases at early stage, the hyperlactatemia and lactate acidemia may not necessarily be detected in the blood, and the excessive lactate production and lactate acidemia may only be confined to the part of affected organ. Since serum LDH elevation often appears much earlier than the hyperlactatemia, LDH testing can be used as a sensitive indicator for excessive lactate production, particularly for local damage, such as an early focal cerebral ischemia, heart ischemia, limb ischemia etc. Serum LDH detection kits are commercially available in clinic. Therefore, preventive treatment can be initiated for diseases at risk of excessive lactate production and lactate acidemia in accordance with LDH testing results.

The following diseases invariably have excessive lactate production, therefore all of them can be treated by the instant invention, and their lactate acidemia is categorized into type A and type B.

Type A lactate acidemia is caused by diseases of inadequate oxygen delivery, which includes almost all critically ill diseases. Critically ill diseases are life-threatening illnesses that need immediate treatment. They are often associated with elevated catecholamine secretion inside body as a stress response. Catecholamine, including epinephrine and norepinephrine, is known to cause lactate production. Examples of critically ill diseases include: 1. systemic hypoxia/ischemia diseases, such as cardiac arrest, hemorrhagic shock, heart failure, heart bypass surgery, Chronic obstructive pulmonary disease (COPD); 2. focal ischemia diseases, such as focal cerebral ischemia, focal heart ischemia, intestine ischemia, liver ischemia, kidney ischemia, extremity ischemia; 3. organ system failure/insufficiency, such as respiratory failure, hepatic failure, kidney failure; 4. Various severe infections, such as bacteria sepsis, virus infection; 5. Various traumatic injuries, such as those in head, chest, neck, abdominal, extremities etc., 6. Various crisis of metabolic diseases, such as diabetic ketoacidemia, hyperosmolar hyperglycemic state, thyroid storm; 7. Various severe stress that induce release of catecholamines, such as major surgery (such as heart, lung, brain, kidney, liver, gut, limb etc.), physical and psychological reaction to excessive stimulus, environmental extreme temperature change, burn, over exercise etc.

The ischemia is an interruption of arterial blood supply to tissue, organ or extremity. Restoration of blood flow is known as reperfusion. Ischemia and reperfusion injury occur in tandem and are linked together, often collectively called ischemia/reperfusion injury. Evidence show that the reperfusion produces more lactate than ischemia.

Type B lactate acidemia is caused by none inadequate tissue oxygen delivery. Type B1 diseases include cancer cachexia, leukemia, lymphoma, vitamin deficiency, infection (sepsis is particularly known to induce lactate acidemia), pancreatitis. Type B2 diseases include drug overdose or intoxication caused by drugs or toxins such as biguanides (metformin, phenformin), cyanide, carbon monoxide, beta-agonists, methanol, adrenaline, salcylates, nitroprusside, simvastatin, ethanol intoxication, anti-retroviral drug, anti-cancer chemo therapy drug, acetaminophen, fructose, sorbitol, xylitol isoniazid etc. Type B3 includes genetic diseases with various mitochondria enzyme defects, such as pyruvate carboxylase deficiency, glucose-6-phosphatase and fructose-1,6-bisphosphatase deficiencies, oxidative phosphorylation enzyme defects.

Specifically, although it is contrary to current excitotoxic theory in neuroscience community, glutamine, glutamate and aspartate can be used surprisingly for treating neurological diseases such as brain ischemia, head trauma, spinal cord injury, brain infection etc. Neurological diseases, such as brain ischemia, brain trauma etc., are well known to have excessive lactate production and lactate acidemia. The glutamate, glutamine, aspartate and their combination with MDH, GPDH, AST, ALT and PLP (or vitamin B6) can be administered in neurological patients with excessive lactate production and lactate acidemia.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein can be used to optimize the treatment, e.g., determining the optimum time and/or amount of administration, which will require no more than routine experimentation consisting of monitoring the subject and adjusting the dosage and/or timing.

Specifically, to treat patients with excessive lactate production and lactate acidemia caused by ischemia/reperfusion injury, the timing of administration is believed to be very important. Recent years, thrombolytic therapy (such as tissue plasminogen activator, tPA), percutaneous aspiration thrombectomy, angioplasty and stenting have become the major approaches to restore blood flow. These approaches however, invariably induce ischemia/reperfusion injury leading to controversial clinical results. For examples, it has been reported that the heart and brain ischemia show limited benefit with thrombus aspiration (Lancet 2016, 9:387, Lancet 2012, 380:1231-40; Lancet 2012, 380:1241-9, Circ Cariovasc Intery 2015, 8:e002258, J Neurointery Surg 2013, 5(Suppl 1):i74-6; J Neurointery Surg 2010; 2:341-4; J Neurointery Surg 2014; 6:77-80). The inventor surprising found that, to be effective, the instant pharmaceutical composition should be used as a treatment prior to the restoration of blood flow. Preferably, the treatment using the present composition described herein lasts for a suitable period, for example, 5 minutes to 3 hours to allow ischemia issue to generate enough ATP, before restoring blood flow.

The dosage of any pharmaceutical compositions of the present invention will vary depending on the symptoms, age and body weight of the patient, the nature and severity of the disorder to be treated or prevented, the route of administration, and the form of the subject composition. Any of the subject formulations can be administered in a single dose or in divided doses. Dosages for the pharmaceutical compositions of the present invention can be readily determined by techniques known to those of skill in the art or as taught herein.

An effective dose or amount, and any possible effects on the timing of administration of the formulation, may need to be identified for any particular composition of the present invention. This can be accomplished by routine experiment as described herein, using one or more groups of animals (preferably at least 5 animals per group), or in human trials if appropriate. The effectiveness of any subject composition and method of treatment or prevention can be assessed by administering the composition and assessing the effect of the administration by measuring one or more applicable indices, and comparing the post-treatment values of these indices to the values of the same indices prior to treatment.

While the subject is being treated, the health condition can be monitored by measuring one or more of the relevant indices at predetermined times during the treatment period, for examples, lactate and pH value, glutamate, aspartate, AST, ALT, MDH and LDH level in blood. The LDH increase is associated with excessive lactate production. Therefore, LDH level can be used as an indicator of excessive lactate production. Treatment, including composition, amounts, times of administration and formulation, can be optimized according to the results of such monitoring. The patient can be periodically reevaluated to determine the extent of improvement by measuring the same parameters. Adjustments to the amount(s) of subject composition administered and possibly to the time of administration can be made based on these reevaluations.

Treatment can be initiated with smaller dosages which are less than the optimum dose of the compound. Thereafter, the dosage can be increased by small increments until the optimum therapeutic effect is attained.

The use of the subject compositions can reduce the required dosage for any individual agent contained in the compositions because the onset and duration of effect of the different agents can be complimentary.

Toxicity and therapeutic efficacy of subject compositions can be determined by standard pharmaceutical procedures in cell cultures or experimental animals, e.g., for determining the $LD_{50}$ and the $ED_{50}$ or limit test. Acute toxicity can be assessed using increasing doses in mice and rodents. Exploratory acute toxicity in mice and/or rats after single dose can be undertaken to begin estimation of the therapeutic window of inhibitors and to identify the potential target organs of toxicity. As candidate selection nears, these studies can provide guidance for the selection of proper doses in multi-dose studies, as well as establish any species specific differences in toxicities. These studies can be combined with routine PK measurements to assure proper dosages were achieved. Generally, 3-4 doses will be chosen that are estimated to span a range having no effect through to higher doses that cause major toxic, but non-lethal, effects. Animals will be observed for effects on body weight, behavior and food consumption, and after euthanasia, hematology, blood chemistry, urinalysis, organ weight, gross pathology and histopathology will be undertaken.

EXEMPLIFICATION

The invention now being generally described, it will be more readily understood by reference to the following examples which are included merely for purposes of illustration of certain aspects and embodiments of the present invention, and are not intended to limit the invention in any way.

Example 1: Effect on Lactate Production and Lactate Acidemia in Cardiac Arrest Rat Model Cardiac Arrest Model and CPR Rats weighing between 250-300 g were used. Cardiac arrest was induced in each rat as follow: Ketamine/xylazine 30 mg/kg ip was given for anesthesia. The trachea was incubated and connected to a rodent ventilator (tidal volume 2.3 ml, rate 50/min). The body temperature was kept constant at 37±1° C. with a heating blanket. By local cut-down procedures, each rat underwent placement of a saline-filled right femoral artery and right femoral vein catheter (PE-50). Mean arterial pressure (MAP) was continuously monitored through arterial catheter. Electrocardiographic (ECG) was recorded using subcutaneous needle electrodes. Cardiac arrest was induced by electrical stimulation (alternating current:12 V, 50 Hz) via the esophageal electrode and an external electrode covered with electrode gel and placed on the animals' chest. Ventilation was stopped and the heating blanket switched off. Complete circulatory arrest was indicated by an abrupt decrease in MAP below 15 mm Hg. Each rat was subjected to 7 minutes of complete cardiocirculatory arrest.

At 7 minutes after cardiac arrest, conventional CPR was carried out as follow: Mechanical ventilation was resumed, and manual closed-chest compressions were performed at a rate of 200 compressions/minute. Epinephrine was administered iv at 0.1 mg/kg and defibrillation was initiated if needed. Only rat with successful return of spontaneous circulation (ROSC) was included in the study.

Treatment

At 10 minutes after ROSC, included rats were divided into following groups and treated according the experimental design as Table 1 (n=8 each group).

TABLE 1

Experimental design

| Groups | Treatment | Dose (intravenously) |
|---|---|---|
| G1 | Control (saline) | 14 ml/kg |
| G2 | Sodium glutamate | 4 g/kg (0.29 g/ml) |
| G3 | AST | 200 Units/kg |
| G4 | ALT | 200 Units/kg |
| G5 | PLP + AST | 200 mg/kg + 200 Units/kg |
| G6 | PLP + ALT | 200 mg/kg + 200 Units/kg |
| G7 | MDH | 200 Units/kg |
| G8 | MDH + AST | 200 Units/kg + 200 Units/kg |
| G9 | Sodium glutamate + MDH | 200 Units/kg + 4 g/kg (0.29 g/ml) |
| G10 | Sodium glutamate + AST | 4 g/kg (0.29 g/ml) + 200 Units/kg |
| G11 | Sodium glutamate + ALT | 4 g/kg (0.29 g/ml) + 200 Units/kg |

TABLE 1-continued

Experimental design

| Groups | Treatment | Dose (intravenously) |
|---|---|---|
| G12 | Sodium oxaloacetate + MDH | 4 g/kg (0.29 g/ml) + 200 Units/kg |
| G13 | Sodium glutamate + Sodium Aspartate | 4 g/kg + 4 g/kg |
| G14 | Sodium oxamate | 100 mg/kg |
| G15 | Lodoxamide tromethamine | 200 mg/kg |

MDH, AST and ALT was from procine heart extract.

Brain Death Score Testing

At 12 hours after ROSC, rats were tested for brain death score according to Table 2.

TABLE 2 brain death score (BDS)

| A. | General behavioral deficit | |
|---|---|---|
| | Consciousness | Normal [10], Stuporous [5], Comatose [0] |
| | Arousal | Eye open spontaneously [3], Eye open to pain [1], No eye opening [0] |
| | Respiration | Normal [6], Abnormal [0], Absent [0]. |
| B. | Brain stem function | |
| | Olfaction | Present [3], Absent [0]. |
| | Vision | Present [3], Absent [0]. |
| | Papillary reflex | Present [3], Absent [0]. |
| | Corneal reflex | Present [3], Absent [0]. |
| | Startle reflex | Present [3], Absent [0]. |
| | Whisker stimulation | Present [3], Absent [0]. |
| | Swallowing | Present [3], Absent [0]. |
| C. | Motor assessment Strength | |
| | (left and right side tested and scored separately | Normal [3], stiff/weak [1] No movement/paralyzed [0] |
| D. | Sensory assessment Pain | |
| | (left and right side tested and scored separately) | Brisk withdrawal with pain [3], weak or abnormal response [1], No withdrawal [0]. |
| E. | Motor behavior | |
| | Gait coordination | Normal [3], Abnormal [1], Absent [0] |
| | Balance on beam | Normal [3], Abnormal [1], Absent [0]. |
| F. | Behavior | |
| | Righting reflex | Normal [3], Abnormal [1], Absent [0] |
| | Negative geotaxis | Normal [3], Abnormal [1], Absent [0] |
| | Visual placing | Normal [3], Abnormal [1], Absent [0] |
| | Turning alley | Normal [3], Abnormal [1], Absent [0]. |
| G. | Seizures | No Seizure [10], General Seizure [0]. |

The range of the BDS: Normal=80, and Brain death=0.

Mortality Rate

Rats were allowed to survive for 24 hours, mortality was calculated in each treatment group.

Serum LDH, Lactate and pH Value Measurement

At 24 hours after ROSC, blood samples were collected, serum lactate, pH value were measured using blood chemistry analyzer. LDH was measured using colorimetric method. For rats did not survive 24 hours, blood samples were collected right before the death for LDH, lactate and pH value measurement.

ATP Measurement

The rats were euthanized after blood collection, the brain, heart, liver and kidney were excised, and homogenized at 0° C. ATP content was measured using luciferase-luciferin luminescence detection assay. For rats did not survive 24 hours, the brain, heart, liver and kidney were also harvested right before the death for ATP content measurement.

Results

Mortality at 24 hours after ROSC is shown in Table 3.

TABLE 3

| Groups | Mortality |
|---|---|
| G1: Control (saline) | 8 out of 8 |
| G2: Sodium glutamate | 1 out of 8 |
| G3: AST | 0 out of 8 |
| G4: ALT | 0 out of 8 |
| G5: PLP +AST | 0 out of 8 |
| G6: PLP + ALT | 0 out of 8 |
| G7: MDH | 0 out of 8 |
| G8: MDH + AST | 0 out of 8 |
| G9: Sodium glutamate + MDH | 0 out of 8 |
| G10: Sodium glutamate + AST | 0 out of 8 |
| G11: Sodium glutamate + ALT | 0 out of 8 |
| G12: Sodium Oxaloacetate + MDH | 0 out of 8 |
| G13: Sodium glutamate + Sodium Aspartate | 0 out of 8 |
| G14: Sodium oxamate | 1 out of 8 |
| G15: Lodoxamide tromethamine | 0 out of 8 |

This indicates that the treatments are very effective in reducing mortality (without treatment, no rat can survive for 12 hours; with treatment, all survive for 12 hours, except one rat in sodium glumate and one rat in sodium oxamate treatment.

Brain death score at 12 hours after ROSC is shown in FIG. 1. When comparing G1 with other groups, P is less than 0.01. This indicates that all treatments can prevent brain death. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G4 with G6, P is less than 0.05. This indicates that ALT in combination with PLP has synergistic effect. When comparing G7 with G8 and G12, P is less than 0.05. This indicates that MDH in combination with AST or oxaloacetate has synergistic effect.

Figure 2:
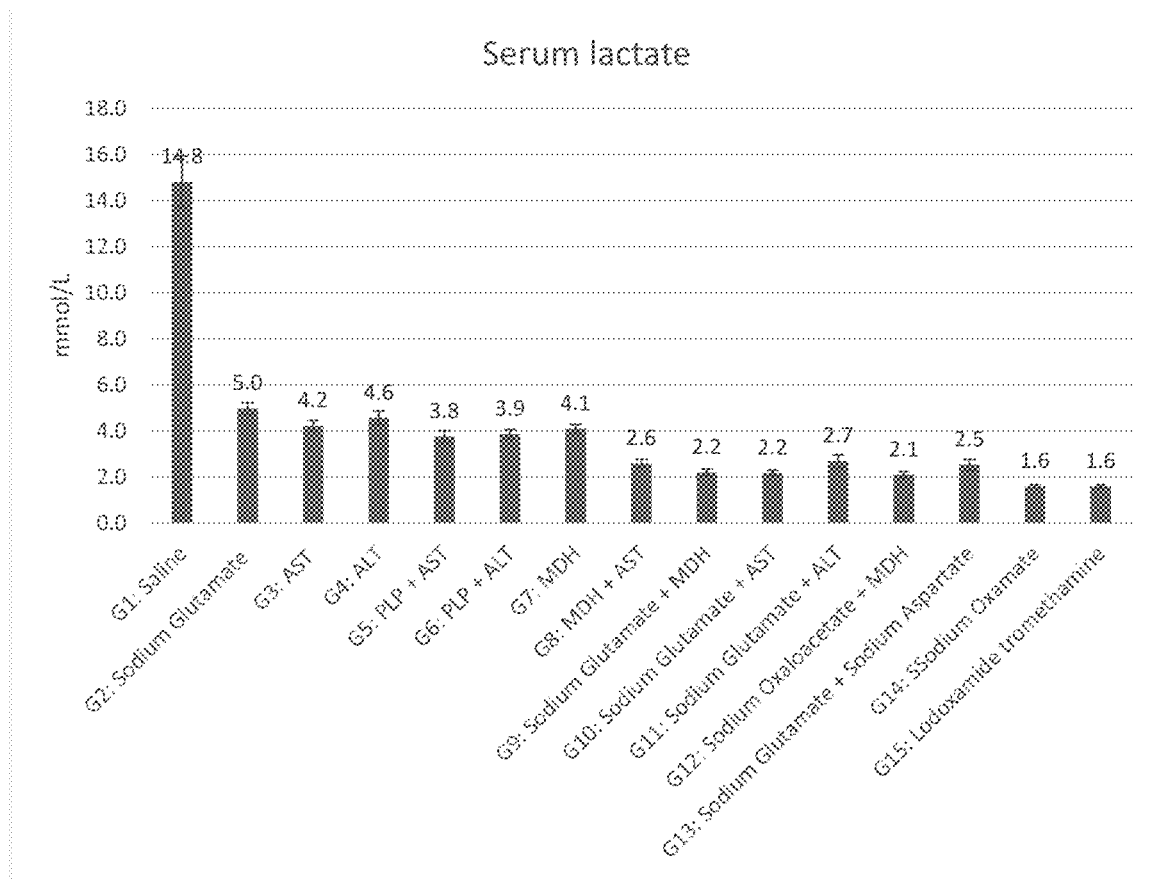
FIG. 2 is a graph showing the effects of treatment groups G1-G15 on the serum lactate level in a cardiac arrest rat model.

Serum lactate in each group are shown in FIG. 2. When comparing G1 with other groups, P is less than 0.01. This indicates that all treatments can reduce serum lactate. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G4 with G6, P is less than 0.05. This indicates that ALT in combination with PLP has synergistic effect. When comparing G7 with G8 and G12, P is less than 0.05. This indicates that MDH in combination with AST or oxaloacetate has synergistic effect.

Figure 3:
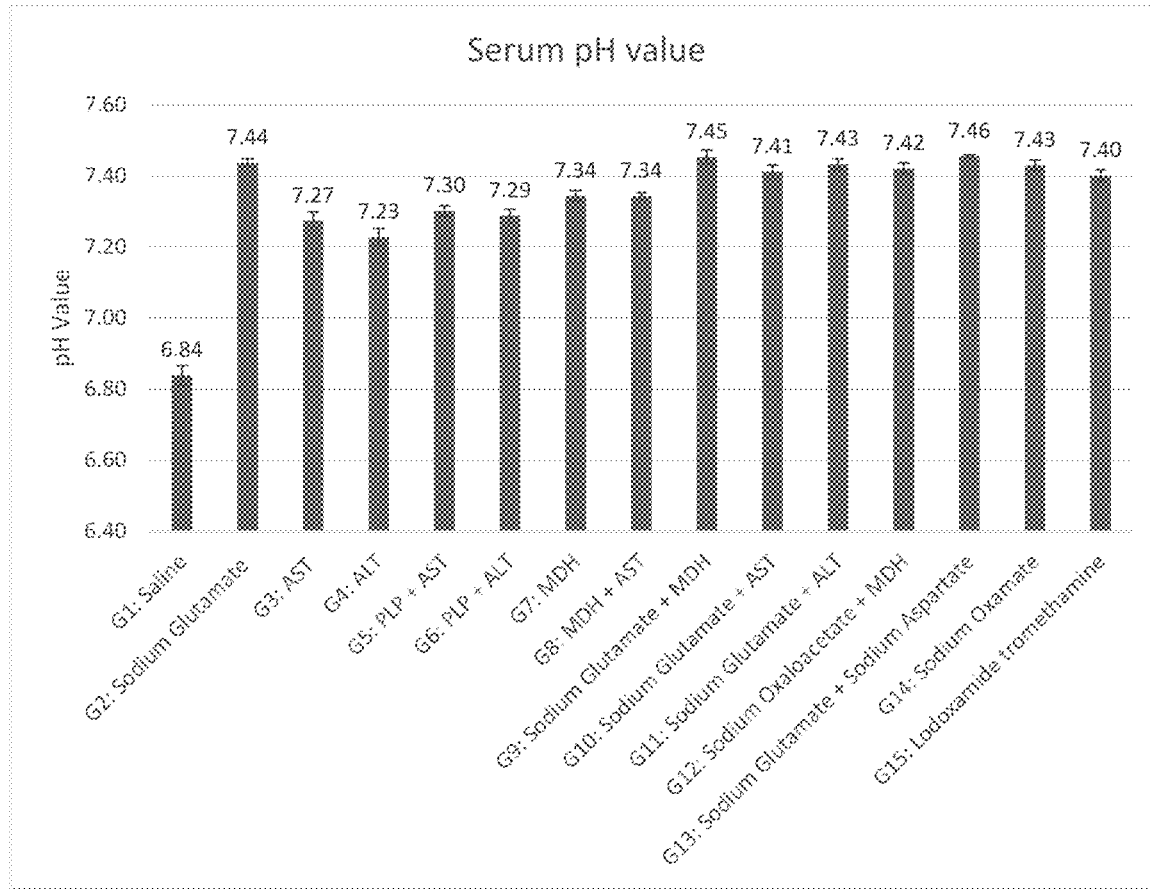
FIG. 3 is a graph showing the effects of treatment groups G1-G15 on the serum pH value in a cardiac arrest rat model.

Serum pH value in each group are shown in FIG. 3. When comparing G1 with other groups, P is less than 0.01. This indicates that all treatment can ameliorate serum lactate acidemia.

Figure 4:
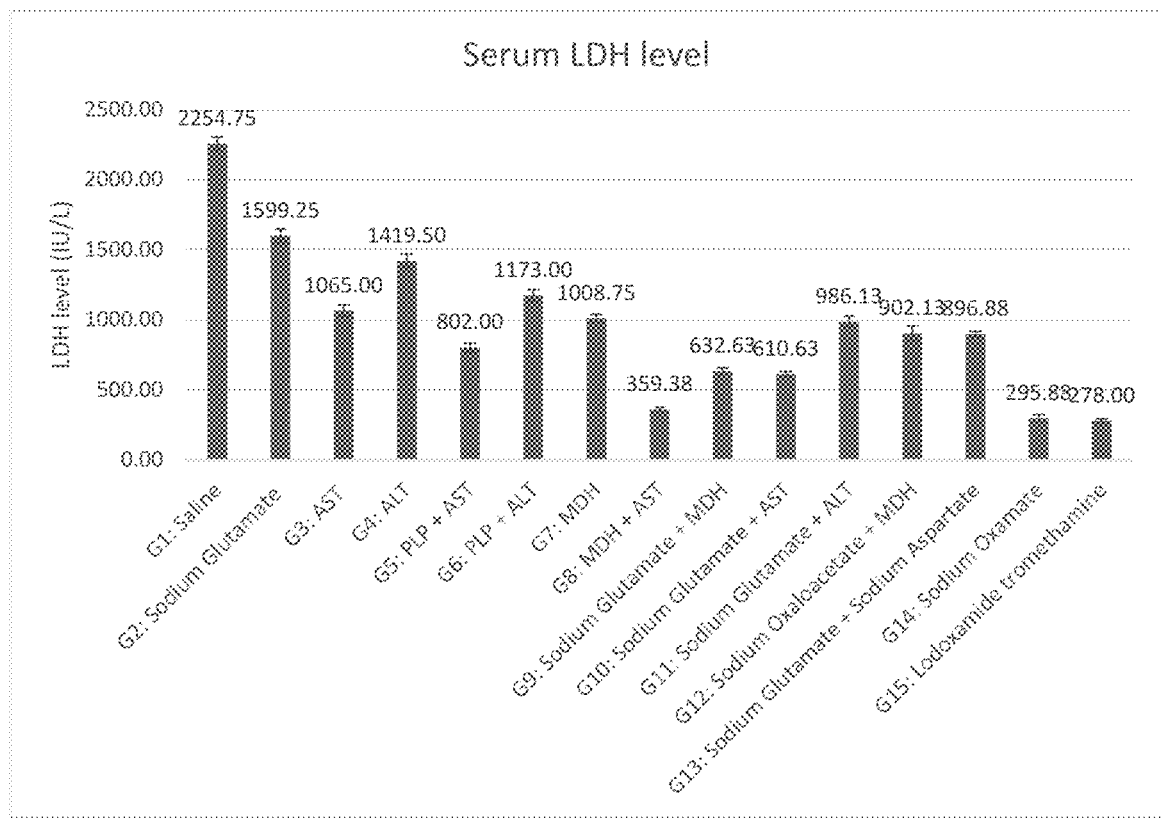
FIG. 4 is a graph showing the effects of treatment groups G1-G15 on the serum lactate dehydrogenase (LDH) level in a cardiac arrest rat model.

Serum LDH activity level in each group are shown in FIG. 4. When comparing G1 with other groups, P is less than 0.01. This indicates that all treatments can reduce serum LDH activity. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G4 with G6, P is less than 0.05. This indicates that ALT in combination with PLP has synergistic effect. When comparing G7 with G8 and G12, P is less than 0.05. This indicates that MDH in combination with AST or oxaloacetate has synergistic effect. This experiment demonstrates that the decrease of serum LDH activity is a new mechanism for the lactate reduction observed in this invention as a result of treatment.

Figure 5:
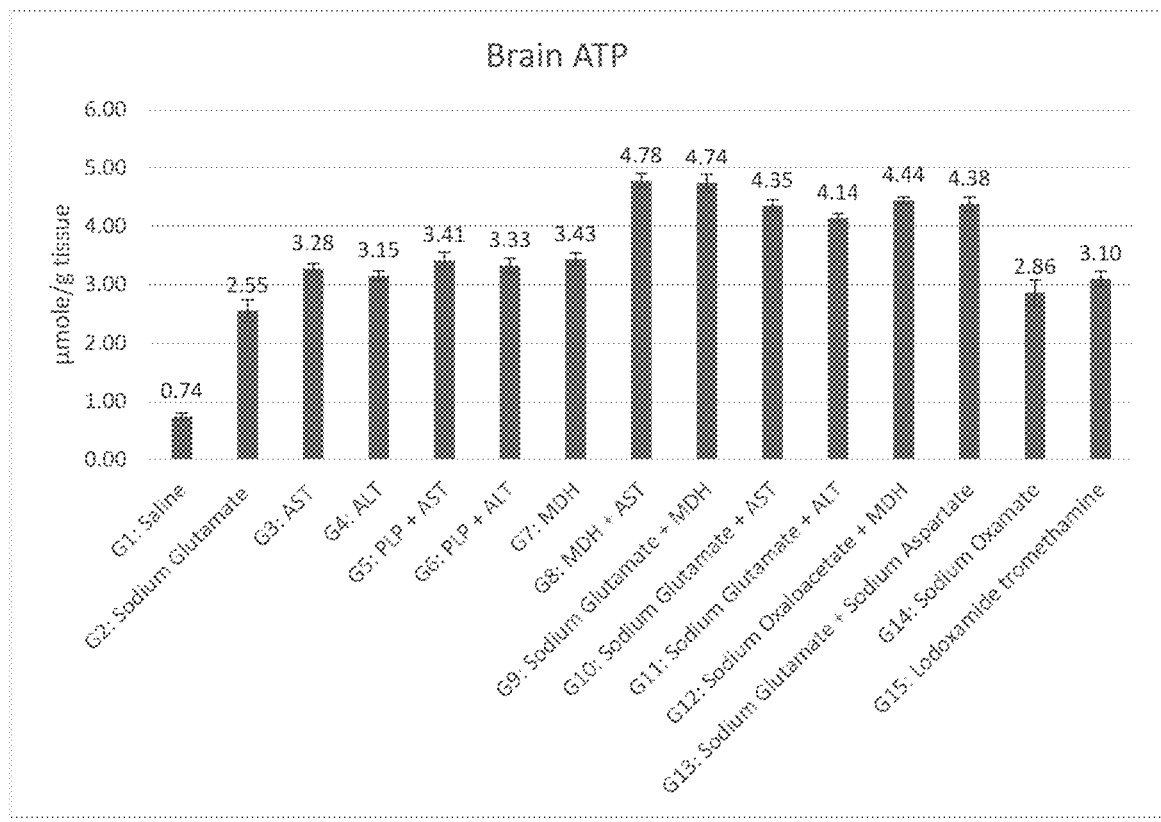
FIG. 5 is a graph showing the effects of treatment groups G1-G15 on the brain ATP level in a cardiac arrest rat model.

Brain ATP content in each group are shown in FIG. 5. When comparing G1 with other groups, P is less than 0.01. This indicates that all treatments can increase brain ATP level. When comparing G2 with G9, G10, G11 and G13, P is less than 0.05. This indicates that glutamate in combination with MDH, AST, ALT or aspartate has synergistic effect. When comparing G3 with G8, P is less than 0.05. This indicates that AST in combination with MDH has synergistic effect. When comparing G7 with G8 and G12, P is less than 0.05. This indicates that MDH in combination with AST or oxaloacetate has synergistic effect. This experiment demonstrates that lactate reduction associated with decreased LDH activity as a result of treatment in this invention can increase brain ATP level.

Figure 6:
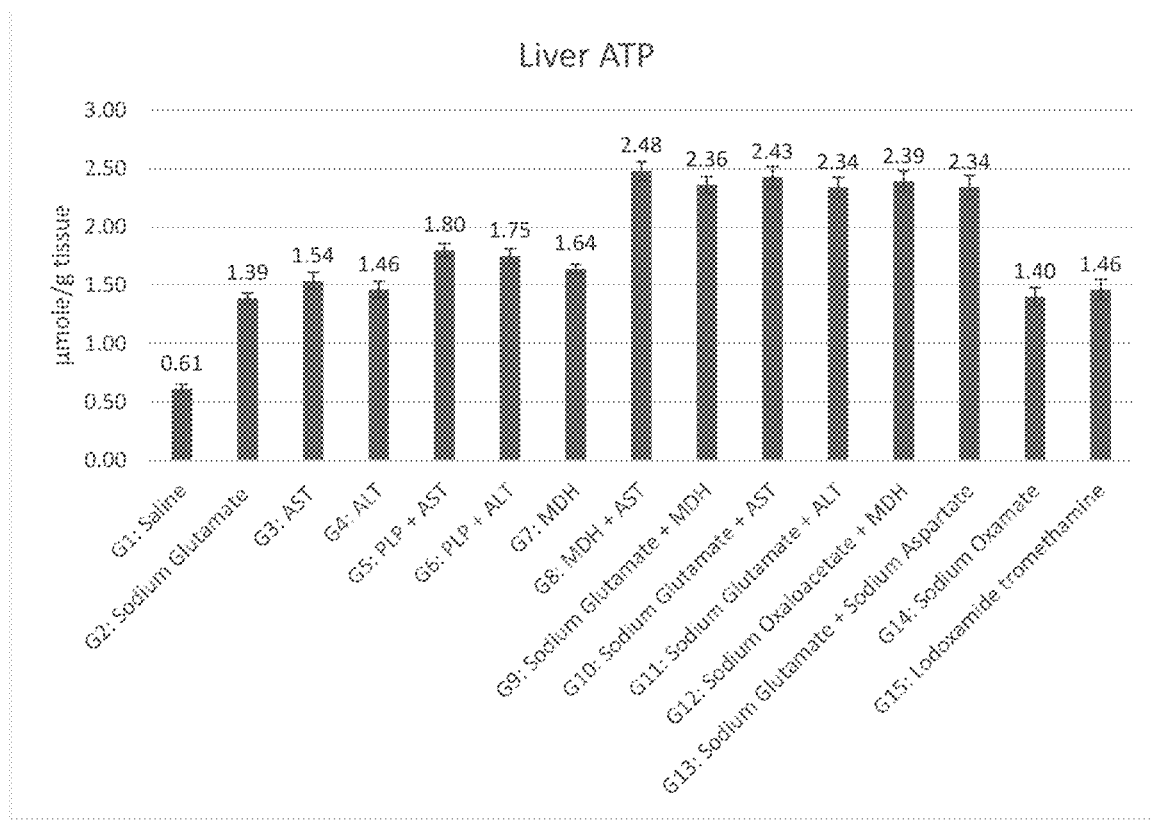
FIG. 6 is a graph showing the effects of treatment groups G1-G15 on the liver ATP level in a cardiac arrest rat model.

Liver ATP content in each group are shown in FIG. 6. When comparing G1 with other groups, P is less than 0.01. This indicates that all treatments can increase liver ATP level. When comparing G2 with G9, G10, G11 and G13, P is less than 0.05. This indicates that glutamate in combination with MDH, AST, ALT or aspartate has synergistic effect. When comparing G3 with G8, P is less than 0.05. This indicates that AST in combination with MDH has synergistic effect. When comparing G7 with G8 and G12, P is less than 0.05. This indicates that MDH in combination with AST or oxaloacetate have synergistic effect. This experiment demonstrates that lactate reduction associated with decreased LDH activity as a result of treatment in this invention can increase liver ATP level.

Figure 7:
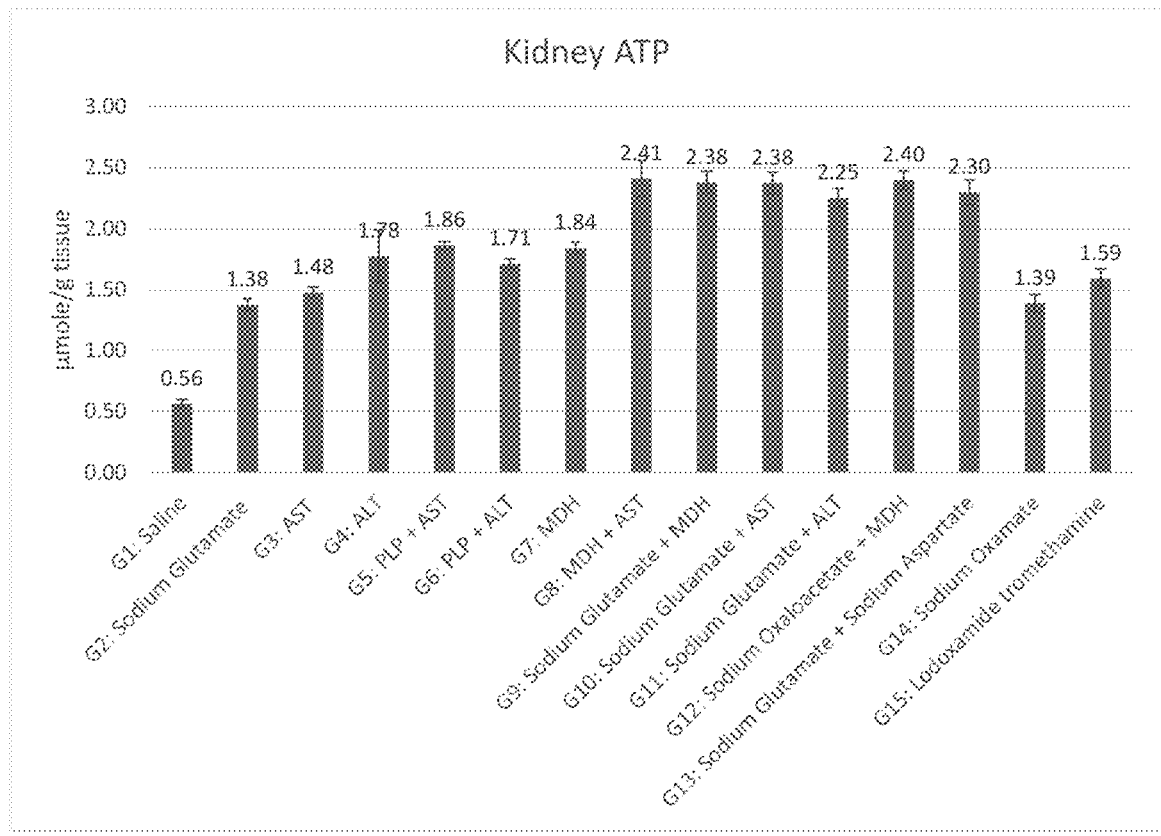
FIG. 7 is a graph showing the effects of treatment groups G1-G15 on the kidney ATP level in a cardiac arrest rat model.

Kidney ATP content in each group are shown in FIG. 7. When comparing G1 with other groups, P is less than 0.01. This indicates that all treatments can increase kidney ATP level. When comparing G2 with G9, G10, G11 and G13, P is less than 0.05. This indicates that glutamate in combination with MDH, AST, ALT or aspartate has synergistic effect. When comparing G3 with G8, P is less than 0.05. This indicates that AST in combination with MDH has synergistic effect. When comparing G7 with G8 and G12, P is less than 0.05. This indicates that MDH in combination with AST or oxaloacetate has synergistic effect. This experiment demonstrates that lactate reduction associated with decreased LDH activity as a result of treatment in this invention can increase kidney ATP level.

CONCLUSION

The pharmaceuticals in this invention, such as glutamate, aspartate, oxaloacetate, AST, ALT, PLP, MDH, Oxamate and Lodoxamide reduce lactate production, correct lactate acidemia in critically ill patient, such as cardiac arrest. The combinations have synergistic effect. The mechanisms are that these pharmaceuticals inhibit (or down-regulated) LDH activity, leading to lactate reduction, and ameliorating acidemia, hereby resulting in ATP content elevation in vital organs (such as brain, liver and kidney), hence ameliorate brain death score, decrease the mortality.

Example 2: Effects on Lactate Production in Focal Cerebral Ischemia Rat Model Cerebral Ischemia Model 180-230 g CD rats were used. Ketamine/xylazine 30 mg/kg ip was given for anesthesia in each rat. A midline incision on the neck was made. The left common carotid artery, the external carotid artery (ECA) and the internal carotid artery (ICA) were exposed. The ECA was ligated and severed. Focal cerebral ischemia was produced by a 3.0 nylon suture that was advanced from the ECA to ICA to block the origin of left middle cerebral artery. The nylon suture was left in place to induce focal cerebral ischemia on left hemisphere supplied by middle cerebral artery. The ischemia lasted for 3 hours, the nylon suture was then removed to allow blood reperfusion for 21 hours.

Treatment

The pharmaceutical treatments were given at 2 hours of ischemia according to experimental design in example 1 of table 1 (n=8 each group). This treatment time point is one hour before restoring blood flow (reperfusion).

Neurological Deficit Test

At 24 hours after cerebral ischemia, each rat was evaluated for behavioral deficits. A score of 0-4 was used to assess the motor and behavioral changes. Score 0: No apparent deficits, Score 1: Contralateral forelimb flexion, Score 2: Decreased grip of the contralateral forelimb when the tail is pulled, Score 3: Spontaneous movement in all directions; contralateral circling only if pulled by tail and Score 4: Spontaneous contralateral circling.

Serum Lactate and LDH Measurement

At 24 hours after ischemia, blood samples were collected, serum lactate, was measured using blood chemistry analyzer. LDH was measured using colorimetric method.

ATP Measurement

After blood samples collection, each rat was euthanized. The brain was excised. A small piece of the cortex in ischemic core was obtained, weighed and then homogenized at 0° C. The ATP content was evaluated using ATP content measurement using luciferase-luciferin luminescence detection assay.

Infarction Size

Each brain was immediately cut into 6 coronal sections (1 mm in thickness) and stained with 1% 2,3,5-triphenyltetrazolium chloride (TTC) in PBS solution at 37° C. for 10 minutes. The infarct size was identified as the non-TTC-stained area, the infarction percentage (%) was calculated by the ratio of area of infarction size to area of whole brain.

Figure 8:
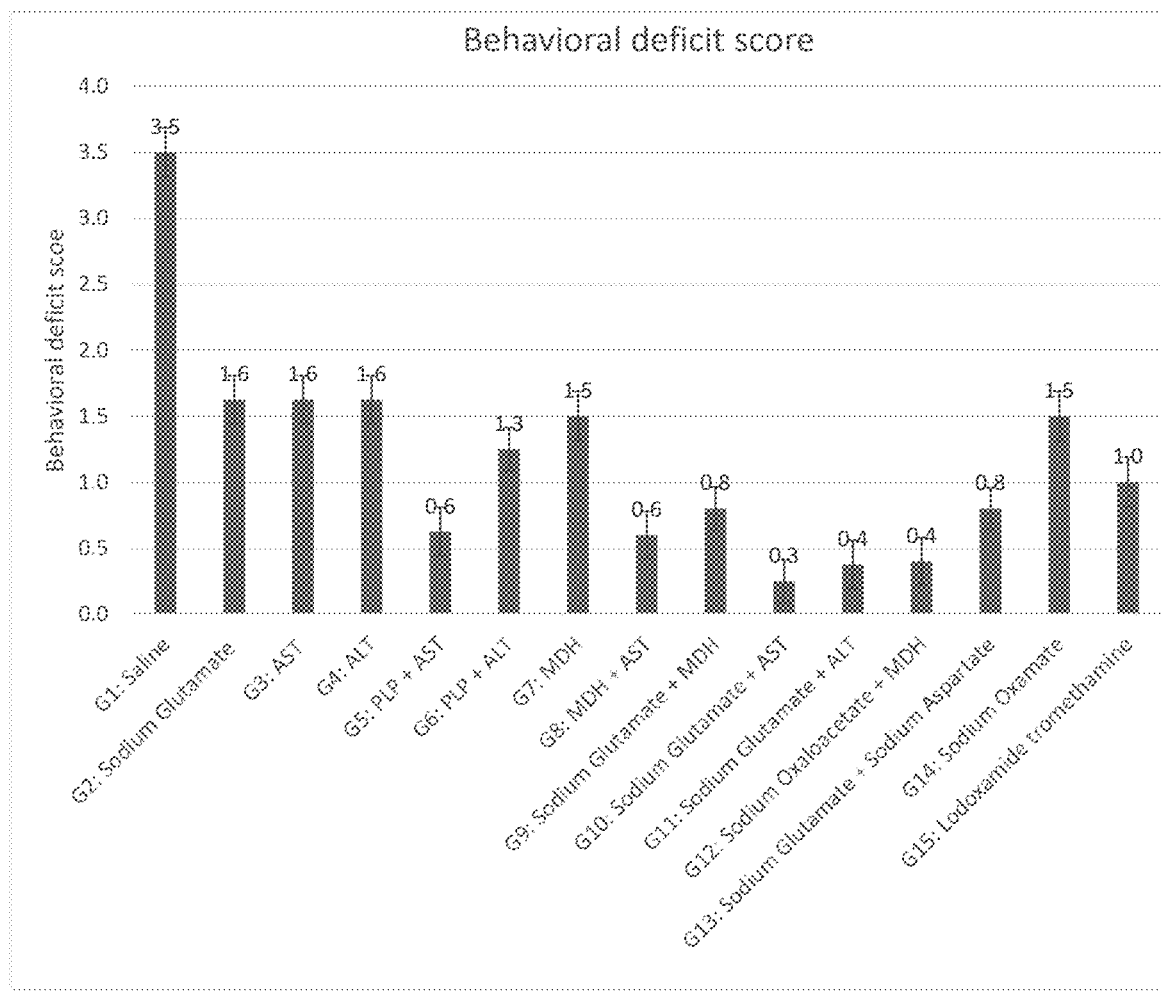
FIG. 8 is a graph showing the effects of treatment groups G1-G15 on the behavioral deficit score in a focal cerebral ischemia rat model.

Results behavioral deficit score is shown in FIG. 8. When comparing G1 with other groups, P is less than 0.01. This indicates that all treatments can improve neurological deficit score. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G7 with G8 and G12, P is less than 0.05. This indicates that MDH in combination with AST or oxaloacetate has synergistic effect.

Figure 9:
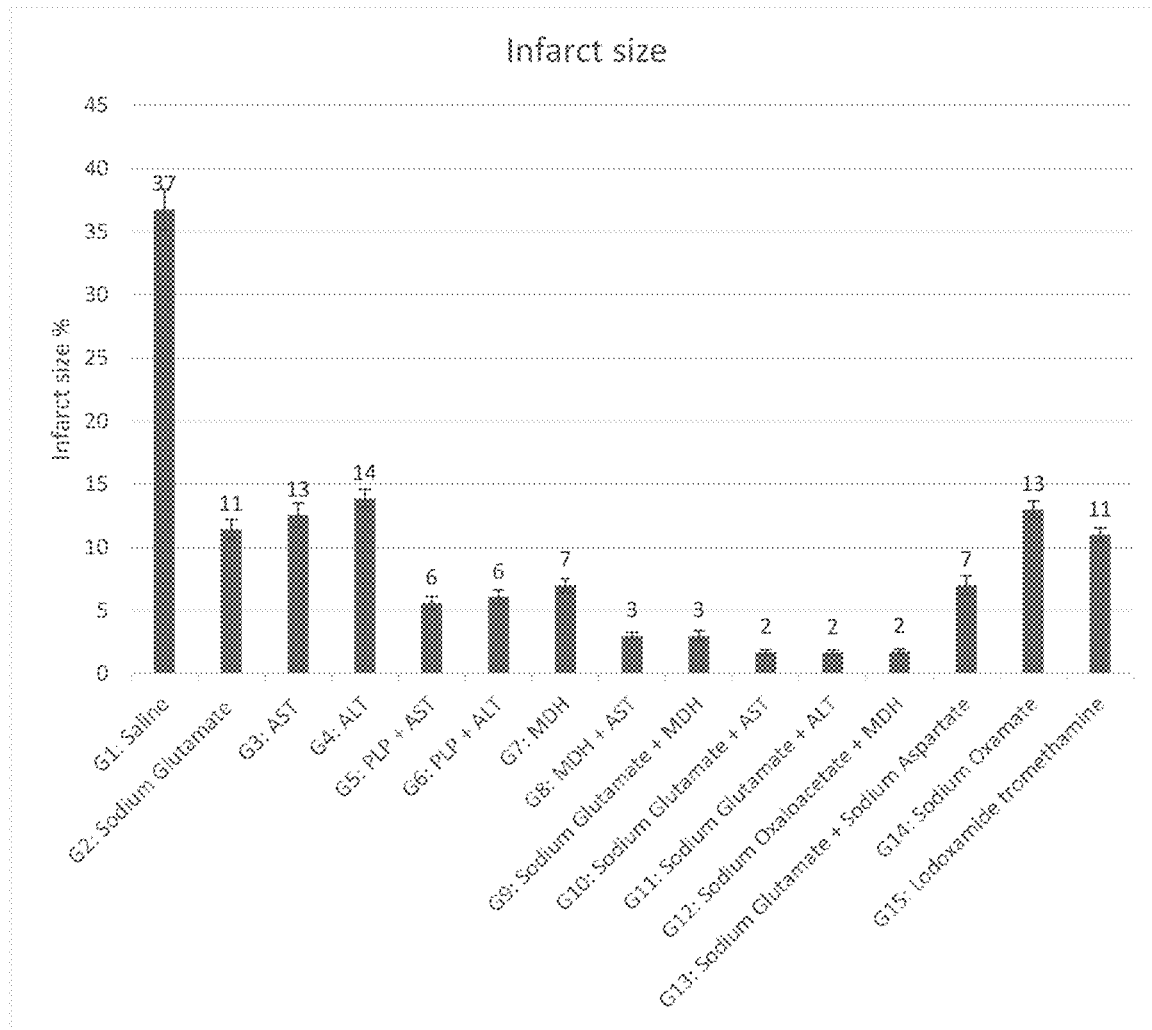
FIG. 9 is a graph showing the effects of treatment groups G1-G15 on the infarct size in a focal cerebral ischemia rat model.

Infarct size is shown in FIG. 9. When comparing G1 with other groups, P is less than 0.01. This indicates that all treatments can reduce cerebral infarct size. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G4 with G6, P is less than 0.05. This indicates that ALT in combination with PLP has synergistic effect. When comparing G7 with G8 and G12, P is less than 0.05. This indicates that MDH in combination with AST or oxaloacetate has synergistic effect.

Figure 10:
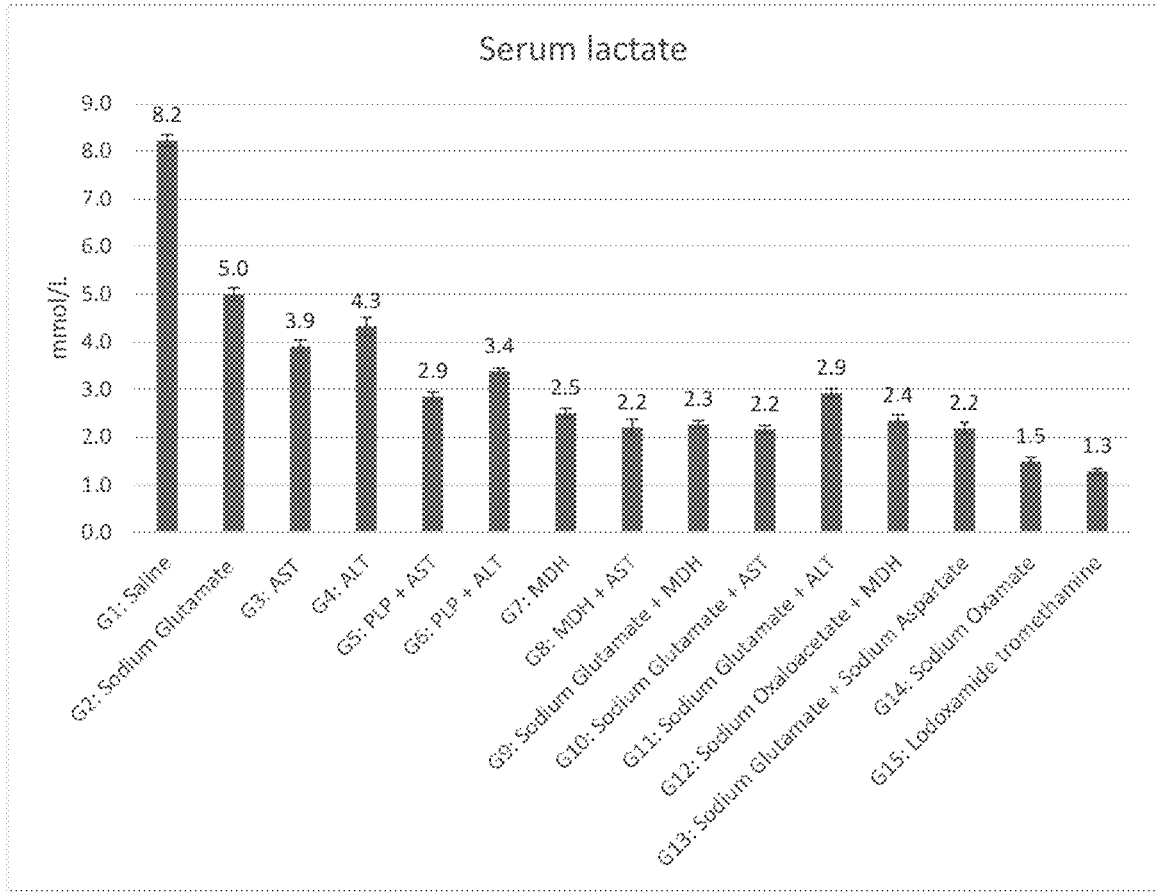
FIG. 10 is a graph showing the effects of treatment groups G1-G15 on the serum lactate level in a focal cerebral ischemia rat model.

Serum lactate content is shown in FIG. 10. When comparing G1 with other groups, P is less than 0.01. This indicates that all treatments can reduce serum lactate. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G4 with G6, P is less than 0.05. This indicates that ALT in combination with PLP has synergistic effect. When comparing G7 with G8 and G12, P is less than 0.05. This indicates that MDH in combination with AST or oxaloacetate has synergistic effect.

Figure 11:
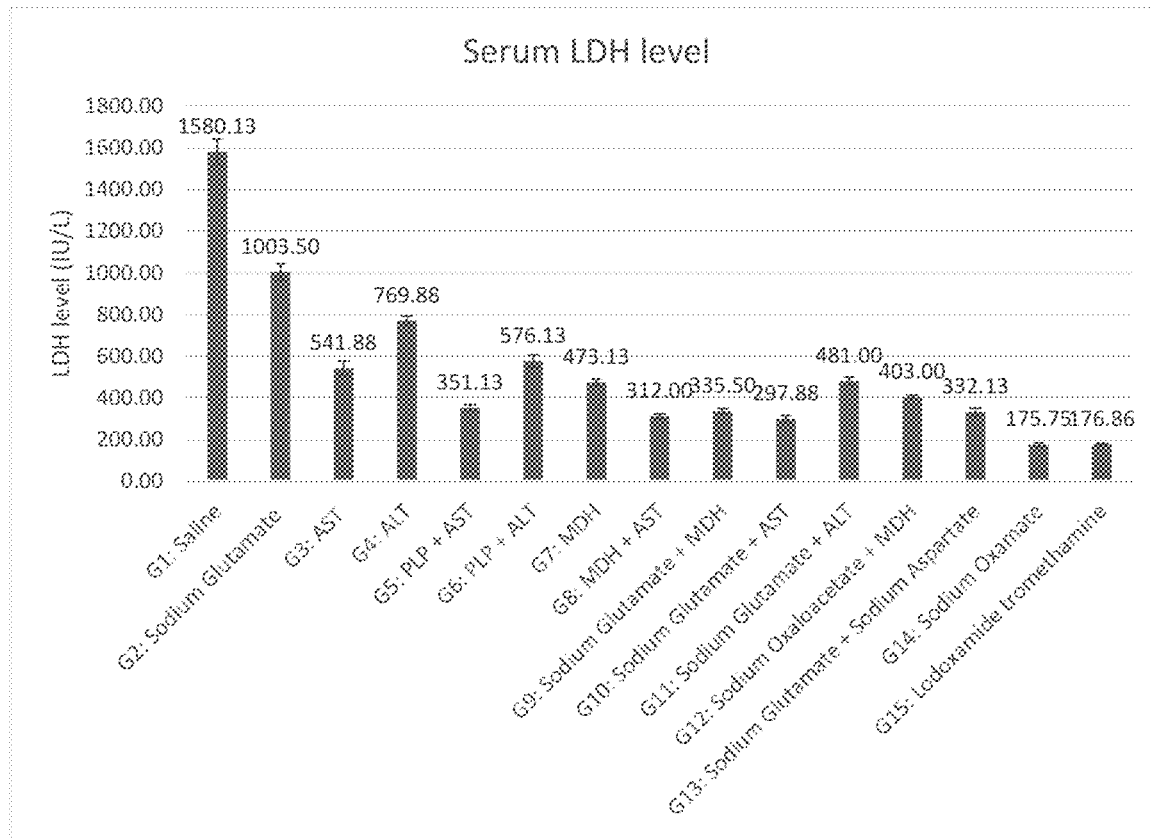
FIG. 11 is a graph showing the effects of treatment groups G1-G15 on the serum lactate dehydrogenase (LDH) level in a focal cerebral ischemia rat model.

Serum LDH content is shown in FIG. 11. When comparing G1 with other groups, P is less than 0.01. This indicates that all treatments can reduce serum LDH activity. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G4 with G6, P is less than 0.05. This indicates that ALT in combination with PLP has synergistic effect. When comparing G7 with G8 and G12, P is 0.05. This indicates that MDH in combination with AST or oxaloacetate has synergistic effect. This experiment demonstrates the decrease of serum LDH activity is a new mechanism for the lactate reduction observed in this invention as a result of treatment.

Figure 12:
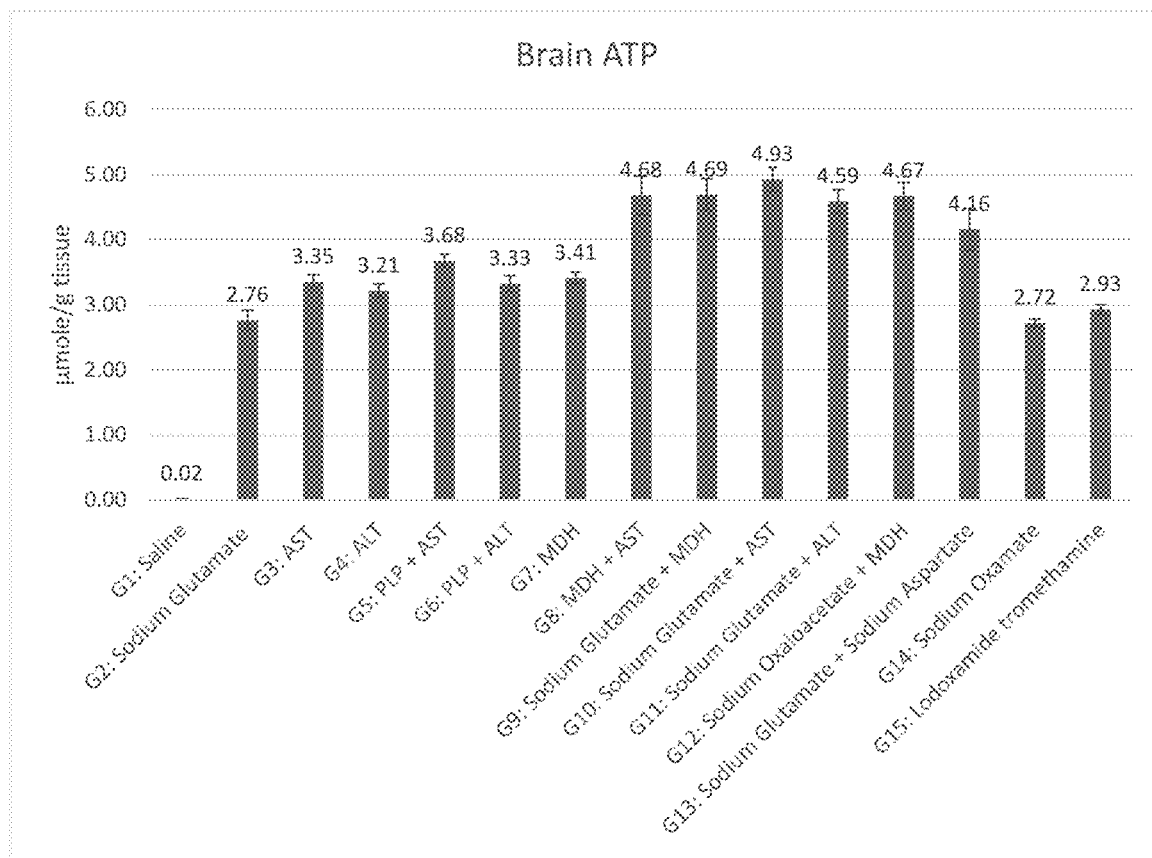
FIG. 12 is a graph showing the effects of treatment groups G1-G15 on the brain ATP level in a focal cerebral ischemia rat model.

Brain ATP content in ischemic region is shown in FIG. 12. When comparing G1 with other groups, P is less than 0.01. This indicates that all treatments can increase brain ATP level. When comparing G2 with G9, G10, G11 and G13, P is less than 0.05. This indicates that glutamate in combination with MDH, AST, ALT or aspartate has synergistic effect. When comparing G3 with G8, P is less than 0.05. This indicates that AST in combination with MDH has synergistic effect. When comparing G7 with G8 and G12, P is less than 0.05. This indicates that MDH in combination with AST or oxaloacetate has synergistic effect. This experiment demonstrates that lactate reduction associated with decreased LDH activity as a result of treatment in this invention can increase brain ATP level. This experiment also shows that the pharmaceutical compositions described herein are effective in reducing lactate production in patients with cerebral ischemia/reperfusion injury.

CONCLUSION

The pharmaceuticals in this invention, such as glutamate, aspartate, oxaloacetate, AST, ALT, PLP, MDH, Oxamate and Lodoxamide reduce lactate production in critically ill patient, such as focal brain ischemia. The combinations have synergistic effect. To treat patient of ischemia/reperfusion injury associated with excessive lactate production, the pharmaceuticals can be used during ischemia period prior to reperfusion. The mechanisms are that these pharmaceuticals inhibit (or down-regulated) LDH activity, leading to lactate reduction, hereby resulting in ATP content elevation in vital organs (such as brain, liver and kidney), hence reduce tissue damage and ameliorate functional deficit.

This experiment also prove that glutamate and aspartate can be used to reduce lactate production in neurological disease despite of the current theory that glutamate and aspartate are excitotoxin.

Example 3: Effect on Intoxication and Severe Lactate Acidemia Induced by Phenformin CD-1 mice (20-25 gram) were used. All mice were pre-treated according to the Table 4.

TABLE 4

| Experimental design (n = 8 each group) | | |
|---|---|---|
| Groups | Treatment | Dose (intravenously) |
| G1 | Control (saline) | 14 ml/kg |
| G2 | Sodium glutamate | 2 g/kg (0.29 g/ml) |
| G3 | AST | 500 Units/kg |
| G4 | ALT | 500 Units/kg |
| G5 | PLP + AST | 400 mg/kg + 500 Units/kg |
| G6 | PLP + ALT | 400 mg/kg + 500 Units/kg |
| G7 | MDH | 500 Units/kg |
| G8 | MDH + AST | 500 Units/kg + 500 Units/kg |
| G9 | Sodium glutamate + MDH | 2 g/kg + 500 Units/kg |
| G10 | Sodium glutamate + AST | 2 g/kg + 500 Units/kg |
| G11 | Sodium glutamate + ALT | 2 g/kg + 500 Units/kg |
| G12 | Sodium Oxaloacetate + MDH | 2 g/kg + 500 Units/kg |
| G13 | Sodium glutamate + Sodium Aspartate | 2 g/kg + 2 g/kg |
| G14 | Sodium oxamate | 300 mg/kg |
| G15 | Lodoxamide tromethamine | 1000 mg/kg |

MDH, AST and ALT was from procine heart extract.

10 minutes after treatment, intoxication of severe lactate acidemia was induced by injecting phenformin chloride (concentration 20 mg/ml) at dose of 200 mg/kg intraperitoneally. At 1 hour after phenformin injection, serum lactate and pH were measured.

Result

Figure 13:
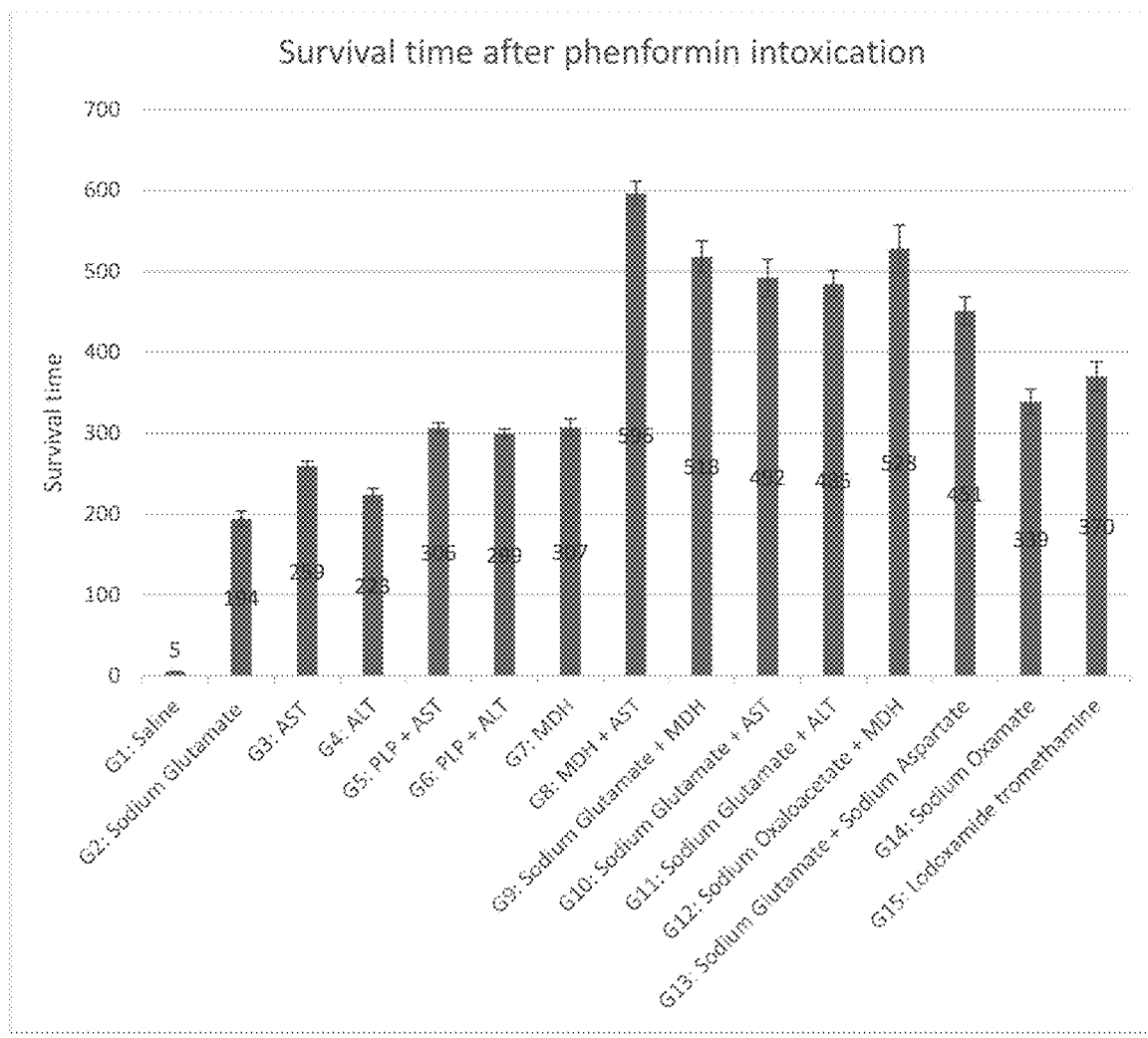
FIG. 13 is a graph showing the effects of treatment groups G1-G15 on the survival time after phenformin intoxication.

Survival time after phenformin intoxication is shown in FIG. 13. When comparing G1 with other groups, P is less than 0.01. This indicates that all treatments prolong the survival time after phenformin intoxication. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G4 with G6, P is less than 0.05. This indicates that ALT in combination with PLP has synergistic effect. When comparing G7 with G8 and G12, P is 0.05. This indicates that MDH in combination with AST or oxaloacetate has synergistic effect.

Figure 14:
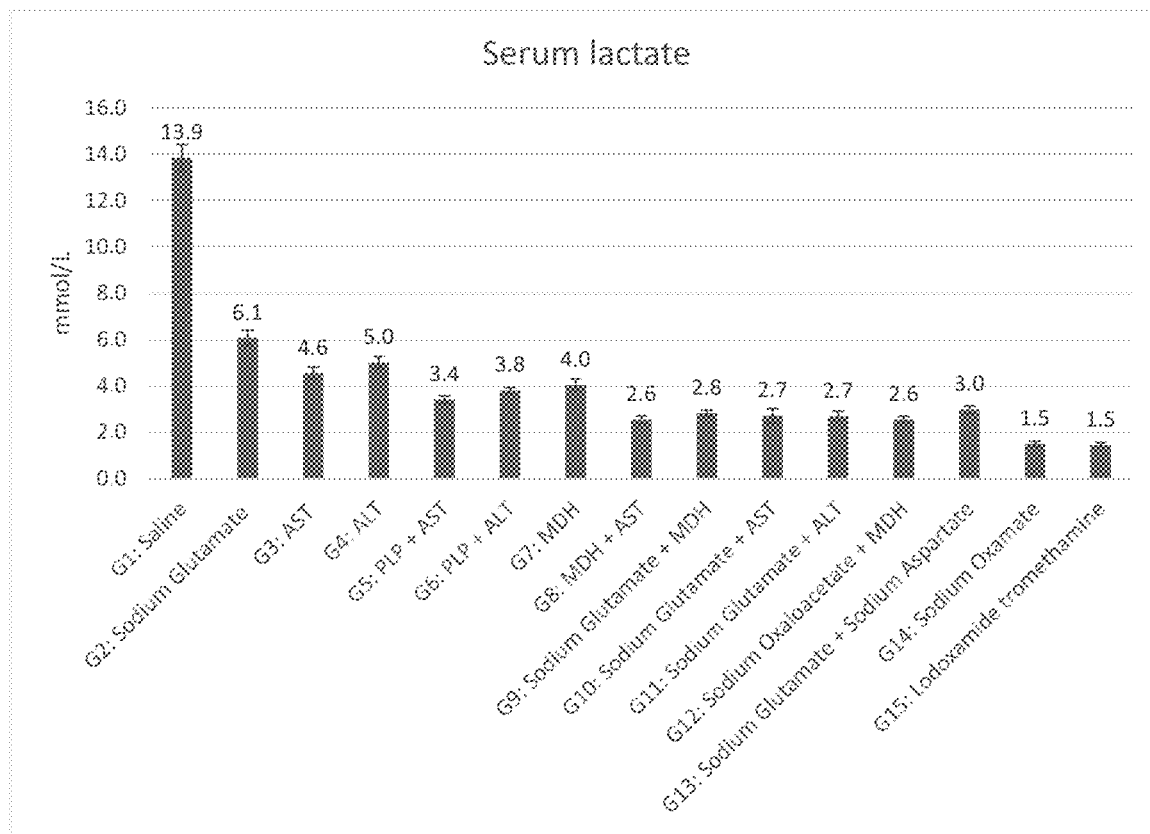
FIG. 14 is a graph showing the effects of treatment groups G1-G15 on the serum lactate level after phenformin intoxication.

Serum lactate at 1 hour after phenformin intoxication is shown in FIG. 14. When comparing G1 with other groups, P is less than 0.01. This indicates that all treatments prevent and counteract excessive lactate production induced by phenformin intoxication. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G4 with G6, P is less than 0.05. This indicates that ALT in combination with PLP has synergistic effect. When comparing G7 with G8 and G12, P is less than 0.05. This indicates that MDH in combination with AST or oxaloacetate has synergistic effect.

Figure 15:
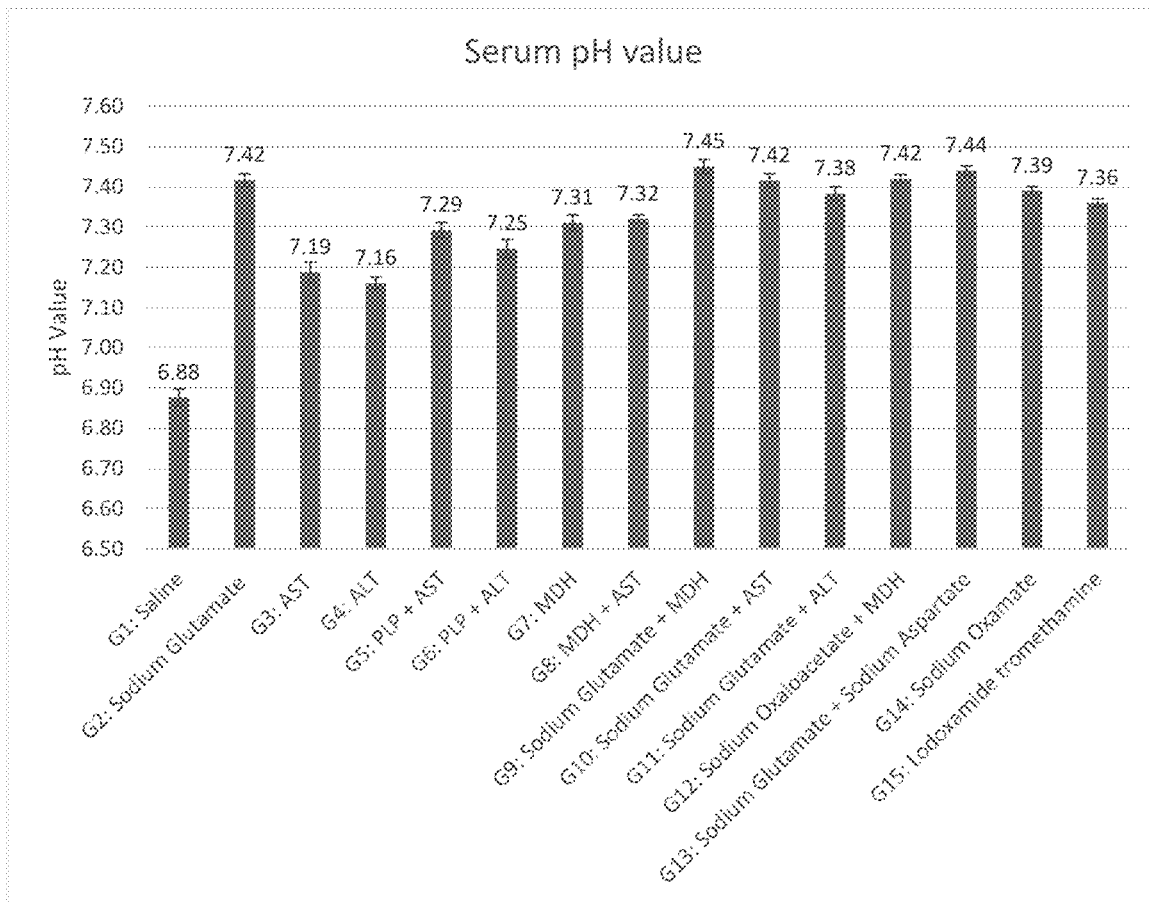
FIG. 15 is a graph showing the effects of treatment groups G1-G15 on the serum pH value after phenformin intoxication.

Serum pH value at 1 hour after phenformin intoxication is shown in FIG. 15. When comparing G1 with other groups, P is less than 0.01. This indicates that all treatments ameliorate serum lactate academia and all treatments can increase pH value by counteracting serum lactate acidemia. Sodium glutamate and sodium aspartate are particularly effective.

Figure 16:
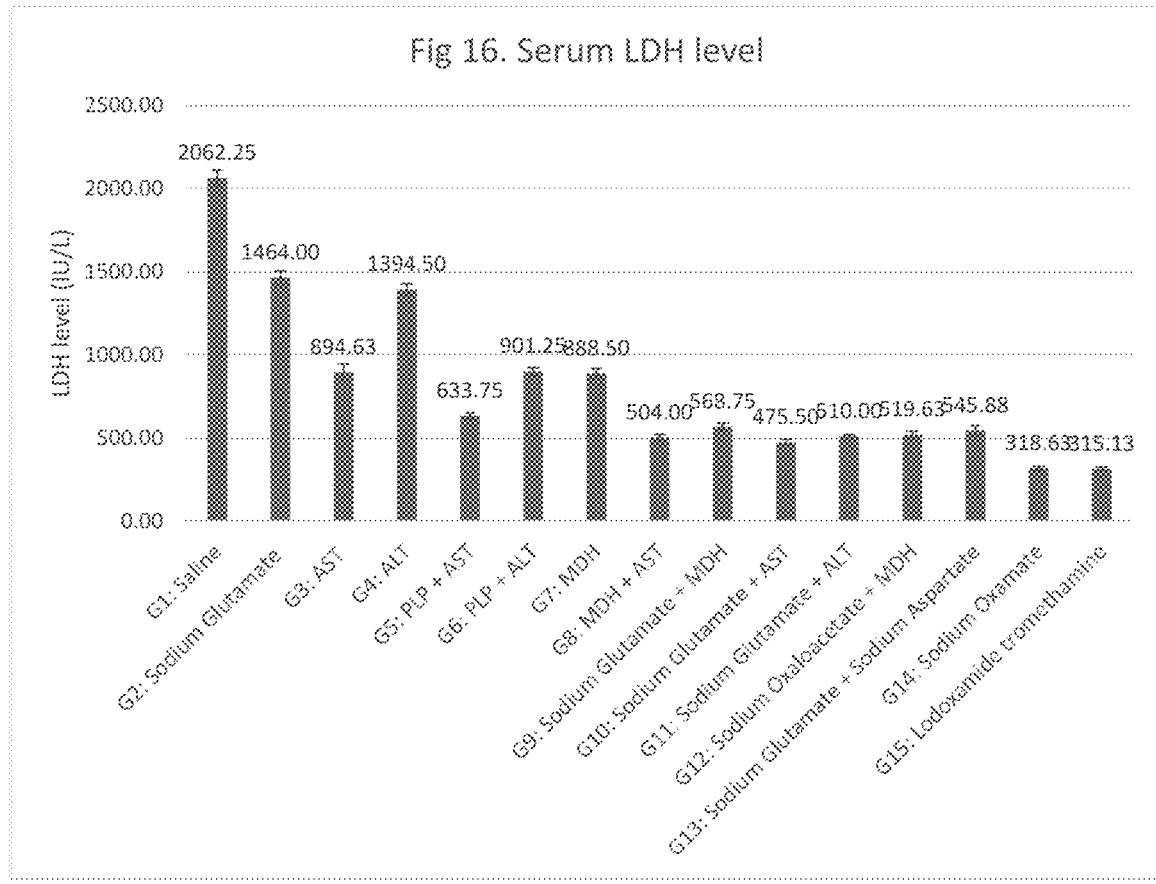
FIG. 16 is a graph showing the effects of treatment groups G1-G15 on the serum lactate dehydrogenase (LDH) level after phenformin intoxication.

Serum LDH at 1 hour after phenformin intoxication is shown in FIG. 16.

When comparing G1 with other groups, P is less than 0.01. This indicates that all treatments can reduce serum LDH activity. When comparing G2 with G9, G10, G11 and G13, P is less than 0.05. This indicates that glutamate in combination with MDH, AST, ALT or aspartate has synergistic effect. When comparing G3 with G5 and G8, P is less than 0.05. This indicates that AST in combination with PLP or MDH has synergistic effect. When comparing G4 with G6, P is less than 0.05. This indicates that ALT in combination with PLP has synergistic effect. When comparing G7 with G8 and G12, P is less than 0.05. This indicates that MDH in combination with AST or oxaloacetate has synergistic effect. This experiment demonstrates that the decrease of serum LDH activity is a new mechanism for the lactate reduction observed in this invention as a result of treatment.

CONCLUSION

The pharmaceuticals in this invention, such as glutamate, aspartate, oxaloacetate, AST, ALT, PLP, MDH, Oxamate and Lodoxamide reduce lactate production, correct lactate acidemia and prolong the survival time in phenformin intoxication. The combinations have synergistic effect. The mechanisms are that these pharmaceuticals inhibit (or down-regulated) LDH activity, reducing lactate production.

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

What is claimed is:

1. A method for treating a patient having excessive lactate production or lactate acidemia, comprising:
    administering to the patient in need thereof an effective amount of at least one substance selected from the group consisting of glutamate, aspartate, BCAA, malate, pyruvate, oxaloacetate, α-ketoglutarate, AST, ALT, PLP, MDH, GPDH, Oxamate, Lodoxamite and salts thereof.

2. The method of claim 1, wherein the substance is sodium or potassium glutamate and the substance is administered at a dosage ranging between 0.001 to 10 g/kg body weight.

3. The method of claim 1, wherein the substance is aspartate and the substance is administered at a dosage ranging between 0.001 to 10 g/kg body weight.

4. The method of claim 1, wherein the substance is BCAA and the substance is administered at a dosage ranging between 0.001 to 10 g/kg body weight.

5. The method of claim 1, wherein the substance is malate and the substance is administered at a dosage ranging between 0.001 to 10 g/kg body weight.

6. The method of claim 1, wherein the substance is pyruvate and the substance is administered at a dosage ranging between 0.001 to 10 g/kg body weight.

7. The method of claim 1, wherein the substance is oxaloacetate and the substance is administered at a dosage ranging between 0.001 to 10 g/kg body weight.

8. The method of claim 1, wherein the substance is α-ketoglutarate and the substance is administered at a dosage ranging between 0.001 to 10 g/kg body weight.

9. The method of claim 1, wherein the substance is AST, ALT, MDH, or GPDH, and the substance is administered at a dosage ranging between 0.0001 ng/kg to 1 g/kg body weight.

10. The method of claim 1, wherein the substance is PLP and the substance is administered at a dosage ranging between 1-100 mg/kg body weight.

11. The method of claim 1, wherein the substance is Oxamate or lodoxamite, and the substance is administered at a dosage ranging between 0.00001-1,000 mg/kg body weight.

12. The method of claim 1, wherein the excessive lactate production or lactate acidemia is caused by:
    Type A: systemic hypoxia/ischemia diseases, such as cardiac arrest, hemorrhagic shock, heart failure, heart bypass surgery, chronic obstructive pulmonary disease (COPD), focal cerebral ischemia, focal heart ischemia, focal intestine ischemia, liver ischemia, kidney ischemia, extremity ischemia, respiratory failure, hepatic failure, kidney failure, bacteria sepsis, virus infection, a traumatic injury to head, chest, neck, abdomin, or extremities, diabetic ketoacidemia, hyperosmolar hyperglycemic state, thyroid storm a surgery to heart, lung, brain, kidney, liver, gut, or limb, physical and psychological reaction to excessive stimulus, environmental extreme temperature change, burn, or over exercise;
    Type B1: cancer cachexia, leukemia, lymphoma, vitamin deficiency, or pancreatitis;
    Type B2: drug over dose or intoxication by a biguanide, cyanide, carbon monoxide, beta-agonists, methanol, adrenaline, salcylates, nitroprusside, simvastatin, ethanol, an anti-retroviral drug, an anti-cancer chemo therapy drug, acetaminophen, fructose, sorbitol, xylitol isoniazid; and
    Type B3: pyruvate carboxylase deficiency, glucose-6-phosphatase or fructose-1,6-bisphosphatase deficiency, or oxidative phosphorylation enzyme defects.

13. The method of claim 1, wherein the excessive lactate production or lactate acidemia is caused by brain ischemia or brain trauma.

14. A method for treating excessive lactate production or lactate acidemia in a patient having ischemia reperfusion injury, comprising:
    administering to the patient in need thereof an effective amount of at least one substance selected from the group consisting of glutamate, aspartate, BCAA, malate, pyruvate, oxaloacetate, α-ketoglutarate, AST, ALT, PLP, MDH, GPDH, Oxamate and Lodoxamite;

restoring blood flow to ischemic region after administering the at least one sub stance.

15. The method of claim 14, wherein the ischemia reperfusion injury occurs in brain.

16. The method of claim 14, wherein the ischemia reperfusion injury occurs in heart.

* * * * *